(12) United States Patent
Breazeale, Jr.

(10) Patent No.: US 9,740,823 B2
(45) Date of Patent: Aug. 22, 2017

(54) HEALTHCARE TRACKING

(76) Inventor: Earl Edward Breazeale, Jr., Louisville, TN (US)

( * ) Notice: Subject to any disclaimer, the term of this patent is extended or adjusted under 35 U.S.C. 154(b) by 109 days.

(21) Appl. No.: 12/165,538

(22) Filed: Jun. 30, 2008

(65) Prior Publication Data

US 2009/0204434 A1 Aug. 13, 2009

Related U.S. Application Data

(63) Continuation-in-part of application No. 11/840,010, filed on Aug. 16, 2007, now abandoned.

(51) Int. Cl.

| | |
|---|---|
| G06Q 10/00 | (2012.01) |
| G06F 19/00 | (2011.01) |
| G06Q 10/06 | (2012.01) |
| G06Q 10/10 | (2012.01) |
| G06Q 30/04 | (2012.01) |
| G06Q 50/22 | (2012.01) |
| G06Q 50/24 | (2012.01) |
| G07C 1/10 | (2006.01) |

(52) U.S. Cl.
CPC .......... *G06F 19/328* (2013.01); *G06F 19/327* (2013.01); *G06Q 10/06* (2013.01); *G06Q 10/1095* (2013.01); *G06Q 30/04* (2013.01); *G06Q 50/22* (2013.01); *G06Q 50/24* (2013.01); *G07C 1/10* (2013.01)

(58) Field of Classification Search
CPC ................................ G06Q 10/00; G06Q 30/02
USPC .................................. 705/2, 3, 7.11–7.42, 4
See application file for complete search history.

(56) References Cited

U.S. PATENT DOCUMENTS

| | | | |
|---|---|---|---|
| 6,591,242 B1 * | 7/2003 | Karp et al. .................. | 705/2 |
| 6,678,703 B2 | 1/2004 | Rothschild et al. | |
| 6,790,198 B1 | 9/2004 | White et al. | |
| 6,826,536 B1 | 11/2004 | Forman | |
| 7,313,529 B2 * | 12/2007 | Thompson .................. | 705/3 |
| 7,421,398 B2 * | 9/2008 | Kimmel ...................... | 705/3 |
| 2001/0047286 A1 * | 11/2001 | Walker et al. ............... | 705/9 |
| 2002/0138306 A1 | 9/2002 | Sabovich | |
| 2002/0165733 A1 | 11/2002 | Pulkkinen et al. | |
| 2003/0093298 A1 * | 5/2003 | Hernandez et al. ......... | 705/2 |
| 2004/0102182 A1 | 5/2004 | Reith et al. | |
| 2004/0254816 A1 | 12/2004 | Myers | |

(Continued)

FOREIGN PATENT DOCUMENTS

| | | |
|---|---|---|
| KR | 10-2000-0076025 | 12/2000 |
| KR | 10-2002-0047586 | 6/2002 |

(Continued)

OTHER PUBLICATIONS

International Preliminary Report on Patentability for Application No. PCT/US2008/073497, dated Feb. 16, 2010, 10 pages.

(Continued)

*Primary Examiner* — David Rines
(74) *Attorney, Agent, or Firm* — Fish & Richardson P.C.

(57) ABSTRACT

A computer-implemented method is disclosed. The method includes obtaining location-time data automatically generated by a mobile electronic device associated with a healthcare provider, correlating the location-time data with a location of a healthcare patient, and using the location-time data to bill for care of the healthcare patient by the healthcare provider.

27 Claims, 13 Drawing Sheets

(56) References Cited

U.S. PATENT DOCUMENTS

| | | | |
|---|---|---|---|
| 2005/0149358 | A1 | 7/2005 | Sacco et al. |
| 2005/0192846 | A1 | 9/2005 | De Zwart et al. |
| 2005/0209886 | A1 | 9/2005 | Corkern |
| 2006/0111941 | A1 | 5/2006 | Blom |
| 2006/0155584 | A1 | 7/2006 | Aggarwal |
| 2007/0168229 | A1 | 7/2007 | Kim |
| 2007/0185739 | A1* | 8/2007 | Ober et al. .............. 705/3 |
| 2007/0192133 | A1 | 8/2007 | Morgan |
| 2007/0273517 | A1 | 11/2007 | Govind |
| 2008/0052128 | A1 | 2/2008 | Beraja et al. |
| 2008/0162580 | A1 | 7/2008 | Ben Harush |
| 2009/0048865 | A1 | 2/2009 | Breazeale |
| 2010/0198608 | A1* | 8/2010 | Kaboff et al. ............ 705/2 |

FOREIGN PATENT DOCUMENTS

| | | |
|---|---|---|
| KR | 10-2003-0025242 | 3/2003 |
| WO | 2005/088493 | 9/2005 |
| WO | WO 2009/026238 | 2/2009 |

OTHER PUBLICATIONS

Commissioner Korean Intellectual Property Office, International Search Report/Written Opinion in PCT/US2008/073497 mailed Jan. 30, 2009, 11 pages.

Sangwan et al., "Using RFID Tags for Tracking Patients, Charts and Medical Equipment Within an Integrated Health Delivery Network," *IEEE*, Mar. 19-22, 2005, pp. 1070-1074.

Wu et al., "eWellness: Building a Smart Hospital by Leveraging RFID Networks," *Proceedings of the 2005 IEEE Engineering in Medicine and Biology 27th Annual Conference*, Shanghai, China, Sep. 1-4, 2004, (4 pages).

Wicks et al., "Radio Frequency Identification Applications in Hospital Environments," *Hospital Topics*, 2006, Health Module p. 3 (6 pages).

Wang et al., "RFID applications in hospitals: a case study on a demonstration RFID project in a Taiwan hospital," *Proceedings of the 39th Hawaii International Conference on System Sciences*, 2006 (10 pages).

Fry et al., "Mascal: RFID Tracking of Patients, Staff and Equipment to Enhance Hospital Response to Mass Casualty Events," *AMIA 2005 Symposium Proceedings*, pp. 261-265.

Stankovic et al., "Wireless Sensor Networks for In-Home Healthcare: Potential and Challenges," 2005 (4 pages).

Non-Final Office Action in U.S. Appl. No. 11/840,010 mailed Jun. 1, 2009, 16 pages.

European Search Report & Written Opinion for Application No. EP 08798115.5-2218, dated Sep. 7, 2012, 6 pages.

U.S. Final Office Action in U.S. Appl. No. 11/840,010, dated Feb. 3, 2010, 16 pages.

U.S. Non-Final Office Action in U.S. Appl. No. 11/840,010, dated Sep. 2, 2010, 17 pages.

U.S. Final Office Action in U.S. Appl. No. 11/840,010, dated Jul. 20, 2011, 23 pages.

Australian Office Action in Australian Application No. 2008289085, issued Jan. 9, 2013, 3 pages.

Anonymous. "Drug errors: The hospital R.Ph's story," Drug Topics Advanstar Communications, Inc. 1997. HighBeam Research. Apr. 6, 2013 http://www.highbeam.com.

Canadian Office Action in Canadian Application No. 2,696,394, dated Mar. 21, 2016, 6 pages.

\* cited by examiner

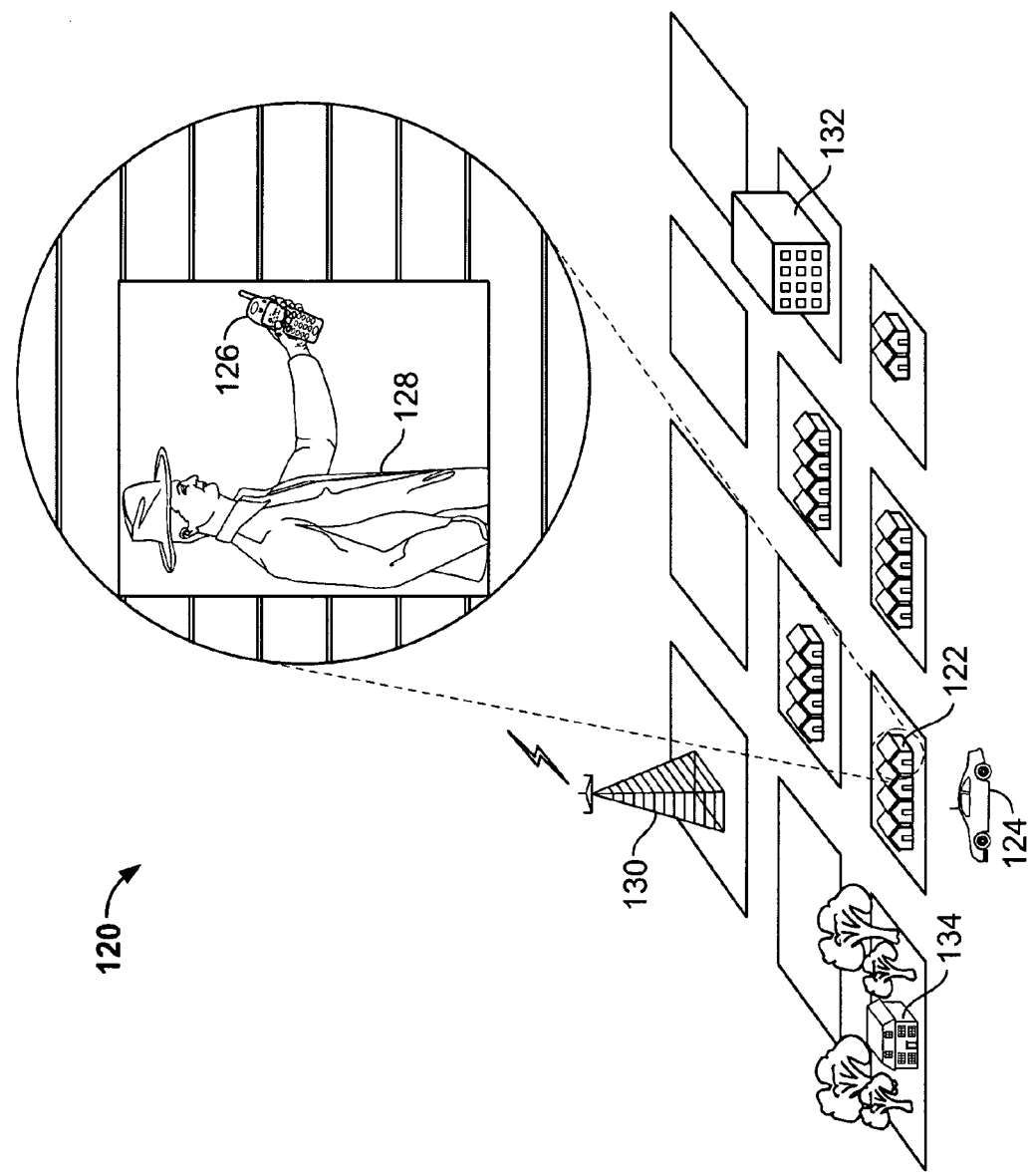

Time Tracker 602

| Object/Patient | Procedure | Start Time | End Time |
|---|---|---|---|
| 042367 | 423-038 | 07.03.01 12:00 | 07.03.01 13:00 |
| 031333 | 611-001 | 07.03.01 12:00 | 07.03.01 14:04 |
| 921027 | 612-002 | 07.03.01 12:02 | 07.03.01 12:04 |
| ... | ... | ... | ... |

614

Billing System 606

| Patient | Charge |
|---|---|
| 042367 | 1110-42-0303 |
| 042367 | 1370-00-1234 |
| 042367 | 1234-56-7890 |
| 042367 | 4682-86-2468 |
| ... | ... |

616

| Patient | Procedure |
|---|---|
| 042367 | 23-12345 |
| ... | ... |

618

| Charge | Cost 1 | Cost 2 | Cost 3 |
|---|---|---|---|
| 1110-42-0303 | 12,500 | 10,000 | 11,252 |
| 1370-00-1234 | 14 | 12 | 15 |

620

Object Tracker 604

| Object | Location | Time |
|---|---|---|
| 042367 | 00102 | 2007-3-1 21:00:02(-6) |
| 042367 | 00104 | 2007-3-1 21:04:01(-6) |
| 042367 | 11213 | 2007-3-1 21:07:22(-6) |
| ... | ... | ... |

608

| Location | Name |
|---|---|
| 00102 | Patient Room 102 |
| 00103 | Patient Room 103 |
| 10104 | Nurse Station A-1st Floor |
| ... | ... |
| 11213 | NW Elevator Bank-Ground |

610

| Object | Start | Stop | ID |
|---|---|---|---|
| 042367 | 2007-3-1 | 2007-3-4 | P02341 |
| 042368 | 2007-3-1 | 2007-3-12 | P02342 |
| ... | ... | ... | ... |

HEALTHCARE TRACKING

CROSS-REFERENCE TO RELATED APPLICATIONS

This application is a continuation-in-part application of and claims priority to U.S. application Ser. No. 11/840,010, filed on Aug. 16, 2007.

TECHNICAL FIELD

Various implementations in this document relate generally to tracking status of patients, caregivers, and other items in a healthcare setting, such as for use in billing and auditing operations.

BACKGROUND

Increasing costs for healthcare are turning into a serious drain on our economy. They directly affect many people who cannot afford needed medical care, and they indirectly affect those who can afford healthcare but need to subsidize the system for others. Surgical care is one of the most expensive areas for many patients—with high costs for specialists, assistants, facilities, and goods such as medical devices. Ongoing care—such as physical and occupational therapy—is another area in which costs are often high for many patients, with repeat visits required over many weeks, months, or even years.

Billing errors and fraud are also potential problems in the healthcare field. Healthcare providers perform many different procedures that need to be billed out, from providing aspirin or an IV, to performing a full scale surgery, and providers are often in a poor position to track and record such procedures (e.g., because they are with the patient, busy performing the procedure rather than at a computer terminal recording it). Providers may also tend to multiple patients before being able to enter billing-related information, and may be interrupted by other small or large emergencies during their work.

Patients may be unable to detect or correct billing errors. They may not be able to keep track of every medication they were given, or every test or other procedure that was performed on them. They may also not understand how items are billed in the medical world. Thus, when they get their bill, they may not know what is right and what is wrong. Also, medical bills can be hard to decipher even for short hospital stays that do not involve much testing. In addition, many of the costs in healthcare occur outside the patient's view or when the patient is not attentive. As a result, errors in a bill, whether unintentional or intentional, may go unnoticed by the patient and by the healthcare providers.

SUMMARY

This document describes various techniques and systems for tracking healthcare patients, caregivers, and other objects. In one example, the tracking may enable creating or verifying billing information associated with patients. Such billing information may be time-based information, such as "in" and "out" times for caregivers, by which those caregivers bill their services. The measured times can be correlated to time-based information relating to the patient, e.g., the time at which the patient entered an operating room, a physical therapy room, a recovery room, or when a home-care giver entered a patient's house. Such information may be used to generate bills for the patient (e.g., when a patient or caregiver's location reflects a triggering event for billing purposes) or can be compared against other billing information (e.g., that is obtained from a patient chart or caregiver time entries) to ensure that all of the available time information is as accurate as is practical.

Such techniques may provide for tracking of accurate time for certain procedures, as opposed to the use of relatively inaccurate estimates of time. For example, in the area of anesthesiology, actual entry of the patient into an operating suite or exit of the patient from a pre-op area may be used to compute the time an anesthesiologist spends with the patient, rather than provider-estimated times. In addition, when actual time is tracked and can be recorded even when the caregiver is unable to record it manually, the triggering events for starting and stopping the "clock" may be changed from what is typically used to create bills, such as by using pre-op exit time rather than a time that an anesthesiologist provides a calming mediation. This approach may eliminate problems, such as when delays in finishing one procedure create delays in starting other procedures, and when the starting point for billing is set too early in the process (e.g., at the provision of calming medication) because accurate time was hard to track previously. Where there is a delay by one patient, so that billing would otherwise start too early in the process for later patients, alternative measurement triggers can be used to prevent unnecessary multiple billing.

The particular mechanisms by which time and location information may be gathered can take a variety of forms. As a first matter, time data may be gathered for patients and/or caregivers. For example, a patient in a healthcare facility may be provided a bracelet when they are admitted, in a familiar manner, and that bracelet may include a transponder that is responsive to sensors located throughout the facility. Likewise, caregivers may have transponders included in their ID badges, or transponders may be included in medical equipment (e.g., patient beds) where appropriate. In implementations that occur outside individual facilities, tracking may occur via mobile devices that are equipped with GPS location sensing functionality. For example, a caregiver's smart phone may be loaded with software that reports the device's location when the caregiver is supposed to be at a patient's home, and that can require the caregiver to also verify that they are in the same location.

As a result, the techniques described here may provide accurate time assessments for care given to a patient, and may thus better match the effort expanded on behalf of the patient with the amount paid by the patient. Such techniques can take a burden off of caregivers by making time entry automatic. They may also lessen the risking of billing fraud, and may provide patients with more confidence in the healthcare system. In addition, the techniques may provide for more detailed billing statements for patients, so that patients can more directly track the costs of their care.

In one implementation, a computer-implemented method is disclosed. The method comprises obtaining location-time data automatically generated by a mobile electronic device associated with a healthcare provider, correlating the location-time data with a location for a healthcare patient, and using the location-time data to bill for care of the healthcare patient by the healthcare provider. The method can further comprise obtaining data regarding a location of the patient's residence, and comparing the location-time data to the location of the residence to determine an amount of time the healthcare provider spent at or near the patient's residence. Also, the method can include receiving data, periodically provided by the healthcare provider while at the location of the healthcare patient, indicating that the healthcare provider is operating the mobile electronic device, and correlating the received data with times during which the healthcare provider is scheduled to be at the location of the healthcare patient.

In some aspects, the received data includes a digital image from the location of the healthcare patient. The method can also include providing to the mobile electronic device data for generating a schedule of care, including location information for the healthcare patient. Data for generating multiple schedules of care can also be provided to multiple mobile electronic devices according to a predetermined schedule. Also, correlating the location-time data with a location of the healthcare patient can comprise comparing the location-time data to a location of a scheduled appointment for the healthcare provider during a time indicated by the location-time data in order to determine whether the healthcare provider was at a scheduled location during a sufficient portion of the appointment. In some aspects, the method can also include computing an amount of a billable event based on elapsed time of the healthcare provider at the location of the healthcare patient.

In another implementation, a computer-implemented method is disclosed, and comprises presenting, to a user of a mobile computing device, a schedule for treatment of one or more healthcare patients, generating, with the mobile computing device, location data for the mobile computing device at locations of the one or more healthcare patients, and submitting the location data to a central service for comparison of the location data to locations associated with the one or more healthcare patients, and for generation of billing event information if the comparison indicates that the user of the mobile device was present at the locations of the one or more healthcare patients. Presenting the schedule can comprise presenting on a graphical user interface one or more maps showing the locations of the one or more healthcare patients. The method can also include automatically downloading schedule data for generating the schedule, without intervention by the user. In addition, the method can comprise seeking manual input from the user during a time period when the user is supposed to be at the locations of the one or more patients. The manual input can include biometric input from the user, and can include submitting the biometric data and location data together to the central service for verification that the user was actually at a patient location during a particular time period. In certain aspects, the method also includes receiving from the central service an indication that treatment of a patient at a scheduled location has been confirmed for the user.

In yet another implementations, a computer-implemented performance verification system is disclosed. The system includes a database storing location data representing geographic locations for healthcare patients, a schedule database storing data representing treatment times for the healthcare patients, and a processor programmed to compare the location data with time-location data for healthcare providers so as to determine whether the healthcare patients received care from the healthcare providers, and to trigger one or more billing events for the care. The system can also include an interface to receive historical location information from mobile devices corresponding to the healthcare providers and to provide the location information for comparison with the stored location data.

In certain aspects, the system can also comprise medical record storage for the healthcare patients, and an interface to provide medical record information from the medical record storage to verified healthcare providers over a wireless network. The system may also include an interface programmed to periodically request location information from a plurality of mobile devices associated with the healthcare providers. The system can also include a schedule generator programmed to identify patients in need of care and to produce schedules for the healthcare providers including location information for the healthcare patients.

Another system includes memory storing time-location information for a plurality of healthcare providers in a healthcare system, the time-location information correlating a physical location of a healthcare provider with a time the healthcare provider was at the physical location, memory storing location information for a plurality of healthcare patients, and means for comparing the time-location information to the location information to determine whether healthcare providers gave care to the healthcare patients.

The details of one or more implementations are set forth in the accompanying drawings and the description below. Other features, objects, and advantages will be apparent from the description and drawings, and from the claims.

DESCRIPTION OF DRAWINGS

FIG. 1B is a conceptual diagram showing tracking of a home healthcare worker using a mobile computing device.

FIG. 6 is a conceptual diagram showing example database elements for a healthcare billing system.

Like reference symbols in the various drawings indicate like elements.

DETAILED DESCRIPTION

Figure 1A:
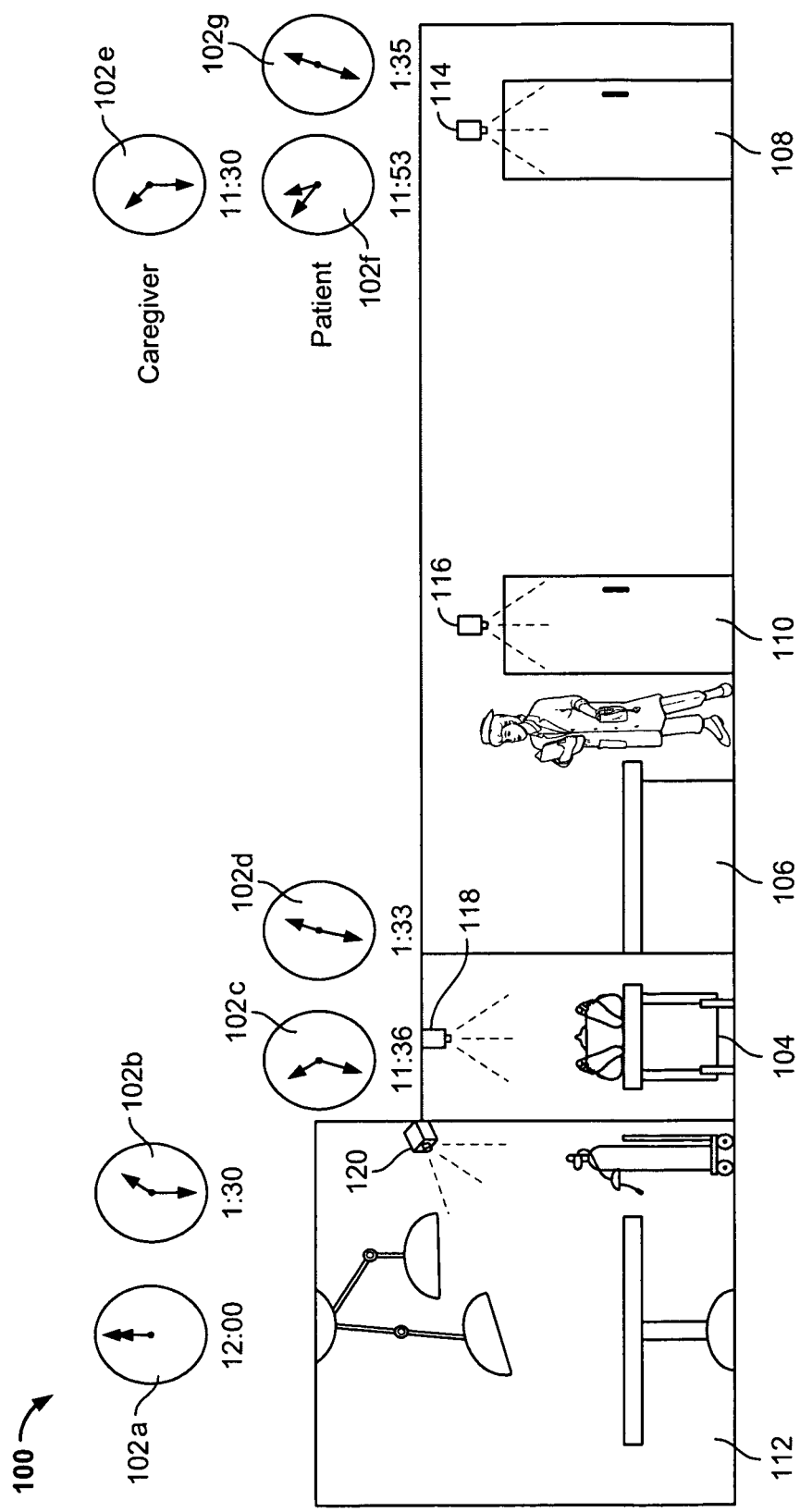
FIG. 1A is a conceptual diagram showing tracking of a patient as part of a surgical procedure.

The systems and techniques described in this document relate generally to tracking patient or healthcare provider locations in a hospital or other healthcare facility or locale, and associating those locations with time. Such time-location data may then be provided to, and/or coordinated with, a healthcare billing system. For example, a transponder such as an RFID tag may be physically associated with a patient (e.g., on a wrist band) and its code may be electronically associated with the patient's records in a computer system. The patient's location may be tracked as the patient passes tracking devices (e.g., RFID sensors) located in a hospital to identify times at which the patient was in the vicinity of such tracking devices. Certain tracking events may be monitored by the system (e.g., entry by the patient into an operating room in which the patient had surgery) and other events may be discarded (e.g., passing the doors of other patient rooms or other operating rooms as the patient moves down a hallway). The relevant tracked time-location data may then be used to determine how long the patient was in certain areas during certain portions of their stay, and that information may be used to produce accurate billing information for the patient.

As one example, certain caregivers bill (or can bill) patients according to time the caregivers spend treating the patients. The tracking and billing coordination techniques described here may be used to provide an accurate and automatic view of how long those caregivers actually spend performing the work. Such data may be used to produce bills for a patient's care, thereby eliminating an administrative timekeeping burden from such caregivers. Or such tracking information may be used as a verification for time that is entered manually or for other billing entries—e.g., as a loose check simply to confirm that a particular procedure actually occurred, or as a more precise check to make sure that manual entries were recorded accurately and that accidental overbilling or underbilling did not occur.

One such exemplary area for time tracking is anesthesiology. There, billing generally occurs according to the AMA's Current Procedural Terminology (CPT) surgery codes that are then associated with American Society of Anesthesiologists (ASA) or Medicare base unit values. Such base units may be used for non-time based billing to assign a billable amount for certain classes of work. In particular, each base unit may be assigned a value, and the cost for a particular procedure may be computed by multiplying the value by the number of base units identified for the procedure. For example, a basic procedure may be identified as a "class 1" procedure, for which four base units may be assigned. The rate for the procedure may be computed easily, and pricing may be negotiated easily for base units without having to also re-determine base units to assign to each type of procedure. Anesthesiology services may also be billed based on time, and other sorts of services that are not currently billed by time, could be so billed if improved time-tracking mechanisms were available. In addition, if more accurate time tracking were available, a globally acceptable anesthesia start time may be formed or adjusted from what is presently used as a start time—as one example, use of pre-op exit time for a patient could be used as a time to start billing, and may provide a more accurate indication of anesthesiologist activity than would earlier times.

FIG. 1A is a conceptual diagram showing tracking of a patient as part of a surgical procedure. The diagram shows, conceptually, a healthcare facility 100 having two patient rooms 108, 110, and an operating room 112 that is part of an operating suite. Various proximity sensors 114-120 are positioned throughout the facility 100 to track movement of objects in the facility. Such systems of sensors may commonly be used to track various objects in a facility for various purposes, such as to allow facility managers to track the location of medical equipment in the facility. As a result, sensors for gathering location data may already be installed in a facility, or the sensors when installed may be used for multiple purposes, so as to lower the effective installed cost of the system. In the implementation described here, the data collected by the tracking system may be accessed and used for other purposes such as for billing.

Various representations of clocks in the figure show the progress of a patient around the time of a surgical procedure. Each clock represents a recognition event by one of the sensors 114-120, caused by a patient-associated transponder moving within range of a particular sensor. The transponder may be located, for example, in a patient ID bracelet, on an IV pole, or in another location attached to the patient or to a piece of equipment associated with the patient. Objects other than the patient may also be tracked by the system. For example, caregivers may be provided with identification badges or other objects containing a transponder that may be recognized by the system. As a result, location and time information for a patient may be correlated with location and time information for one or more caregivers, to provide additional information for billing purposes, and/or to provide confirmatory information for billing purposes.

Clock 102e represents a recognition of a caregiver by sensor 114. The transponder associated with the caregiver may, in response to a signal from sensor 114, transmit a digital message, such as an identification number, that a computer system may associate with the caregiver. The identity of the caregiver, the location of the sensor 114, and the time of the recognition event may all be stored by the tracking system for later access by various other systems. In this example, the caregiver may be an anesthesiologist who had entered a room 108 to provide a patient with a calming medicine before a surgical procedure. Another triggering event may be sensed when the caregiver leaves the room 108, and data for that event may also be stored by the system (though the system may not be able to sense the direction of the caregiver, and may thus infer such direction of the caregiver based on prior locations at which the caregiver has been located, or based on the order of sensing (e.g., someone generally enters a room first and leaves it second)). As explained in more detail below, certain events may be considered triggering events that will be used by other parts of the system (e.g., those needed for billing), while other events may be ignored by the system (e.g., those events that occur when a patient happens to randomly pass by a sensor).

Clock 102f indicates an event that is a patient passing through the door to room 108. The patient may, at that time, be rolled down a hallway, past nursing station 106, and into a hallway of a surgical suite, where the patient's presence is recognized by sensor 118. In moving from room 108 to the surgical suite, the patient may pass room 110, and sensor 116. Such movement may create a triggering event for the system. However, the event may be filtered by the system and not recorded. That is because the passage of a patient past the room of another patient may be considered an event that is not useful to any part of the system, so that storage of such information would be unnecessary.

The filtering may occur, for example, by defining rules for certain objects (e.g., patients, caregivers, or equipment) with respect to the way triggering events for those objects are to be treated. For example, patients may be one class of objects, and each patient may be associated with a particular patient room. Rules may be defined, for example, so that when a triggering event occurs for a patient object with respect to a certain class of locations, such as patient rooms, only triggering events related to the patient room associated with the particular patient are recorded. Other such rules may control the handling of other sensed events.

Other clocks reflect other events surrounding a procedure for the same patient. Clock 102c shows the time of the patient entering the operating room suite, and clock 102a shows the time of the patient entering operating room 112, as determined by sensor 120. Clock 102b shows the time of the patient exiting operating room 112, while clock 102d shows the time of the patient passing sensor 118 while exiting the operating suite. Clock 102g shows the time of the patient reentering patient room 108. In an ordinary example, however, the patient may be moved from operating room 112 to a recovery room and tracked by a sensor there.

By this process, the system has stored a number of time-location pairs that may be associated with a particular patient. The time-location pairs may generally be unassociated with any actions, in that they are simply a time at which a particular sensor was triggered by a transponder associated with an object such as a patient or caregiver, and a corresponding location of the sensor.

However, certain actions regarding a patient may be inferred by combining the time-location information with certain other contextual information. Such contextual information may include information about procedures for which a patient was scheduled, or that were performed on a patient. In such a situation, a system may use time-location information for the patient relating to particular areas the patient would be expected to pass during certain portions of the procedure, to infer that the patient had certain portions of a procedure performed at certain times. For example, the system may be able, by taking the difference in readings between clock 102a and clock 102b, to determine that the patient's operation, which was scheduled around the time of the readings for clock 102a and clock 102b, lasted 1.5 hours. If the spatial range of sensor 120 is too long spatially to differentiate between an entrance to operating room 112 and an exit, because the sensor 120 sensed the patient throughout the time the patient spent in the operating room 112, the signal may be sampled and the start and end times for the presence of the signal may be used to measure the patient's stay, or a sensor farther away from a location in which the patient loiters or passes may be used, such as sensor 118.

As another example, and as explained in more detail above and below, a caregiver such as an anesthesiologist may have their time or actions billed to a patient based on the amount of time the caregiver spends with the patient. The billing clock in such a situation may begin running with the provision of a first medication to the patient or another event, and may end with the patient's entry into a recovery room. In the example shown here, however, the billing period can start based on a location of the caregiver, and can end based on a location of the patient.

In such a situation, when a billing system is preparing charges related to a procedure, or is verifying charges for the procedure, it may look to records related to the patient to identify the particular procedure. Such an inquiry may initially identify the time the procedure was to occur, such as by querying an operating room scheduling system. The billing system may then query a tracking system (such as that discussed above and below) to identify all triggering events for an anesthesiologist that could correspond to the procedure. The system may filter the returned data to identify only relevant triggering events, such as entry by the caregiver into the patient's room during a timeframe before the procedure, such as to begin the administration of medication. The system may likewise query a tracking system for triggering actions related to the patient, such as entry by the patient into a recovery room or into a hallway associated with a recovery suite. The difference between the identified time associated with the caregiver and the identified time associated with the patient may be the billing time range for the anesthesiologist. Alternatively, the start and stop times may be triggered wholly off the patient's locations, off the caregiver's location, or off the locations of multiple caregivers, and only a single time may be used (e.g., simply to confirm that an action occurred so as to permit billing for the action, but not to determine how long the action took).

Such information may be used in a variety of ways. For example, the information may be used to generate a charge for the patient in a first instance, where the accuracy of the time tracking system is sufficiently good. Alternatively, a portion of the information may be used to generate a charge for the patient. For example, an anesthesiologist may record a time to start a billing, while the end of the billing period may be triggered by the sensing of the patient's return to a recovery room. The information gathered by the system may also be used as a check on other information, but not necessarily used to produce the information that drives a billing decision. For example, caregivers may record times at which certain events take place in a traditional manner, and the location data may be used by an audit component of a system to verify that no errors have been made in such recordings. For example, the system may be used to ensure that, where a charge occurs, there actually was a procedure related to that charge (e.g., if a charge is made for surgery or physical therapy, the system may check that the patient actually entered the surgical or physical therapy suite on the appropriate day). Or, a system may look more closely and compare events sensed by the system with times recorded by caregivers to ensure that the times are within a certain level of difference, such as less than five minutes of difference.

The additional contextual information that accompanies a time-location reading for a patient may also be a time-location reading for another object. For example, if a transponder associated with a patient and a transponder associated with a particular caregiver create simultaneous or near simultaneous triggering of a sensor, the activity being performed on the patient may be inferred. For example, if the caregiver is a surgical nurse, then it may be inferred that the patient is heading to/from surgery.

In addition, the time-location information for caregivers may be analyzed to ensure that their billing of time is consistent with certain guidelines. For example, the Centers for Medicare & Medicaid Services (CMS) may have limits on the number of patients that a caregiver may serve and bill simultaneously (e.g., limiting anesthesiologists to four overlapping patients at one time) and may use such time-location information to check compliance with such limits. In particular, location profiles may be generated for each patient that a particular caregiver treated during a given day, with the profiles specifying start and stop times that are computed using data like that above, and a system can check to ensure that no more than four such patients were being treated at one time by a particular caregiver.

Where raw time-location data is stored for a number of patients and a number of caregivers, various forms of post hoc analysis may be performed, with new queries run on the data to produce new analyses. Such analyses may involve analyzing the times for which a patient was receiving active care during a stay at a facility, e.g., by correlating billed events with time-location data for the patient and for various caregivers. This analysis may permit a facility to provide a patient with a report indicating the amount of care they received, so that the patient may better see what he or she received for his or her money. In addition, such information may be tracked for caregivers, to better manage and train caregivers so as to maximize the care they provide and the efficiency of the care they provide. In addition, certain of the time during a patient's stay may be identified in a report as time that there should be no care (i.e., the patient is resting) and other time may be identified as time that there should be care. The actual treatment of the patient may be compared to such a profile to gain a better understanding of whether the patient's treatment was adequate or could be improved.

Moreover, similar data may be accumulated across multiple caregivers in a facility and may be used for benchmarking. For example, certain actions relating to orthopaedic surgery may be analyzed and averaged to provide an indication of the level of care and the efficiency of the care a facility provides. Such analysis may permit the facility to isolate problems in its processes and make them more efficient and/or may permit insurance companies, consumers, or others who are interested in comparing the quality and efficiency of care between facilities to do so. Efficient use of healthcare facilities may also be tracked, such as by determining the level of correlation between scheduled use of procedure rooms and actual use of the rooms, such as to help determine whether such rooms appear full on a schedule but in fact spend much of their time empty. Also, such a system may provide alerts regarding the availability of rooms or equipment, such as by notifying housekeeping when a patient has left their room (e.g., if the patient is sensed as leaving a room around their checkout time) so that the housekeeping staff can immediately begin cleaning the room and readying it for another patient.

The techniques here may also be used in part of a pay-for-performance type of healthcare improvement program. Such a program generally attempts to track the time that a physician or physician group requires to perform a procedure, and the number of complications or other negative events associated with the procedure. The program attempts to award physicians or physician groups that perform quickly or efficiently, while still providing high quality care. More accurate tracking of physician time and other time associated with a patient may permit more accurate tracking of performance in such a pay for performance program.

Certain approaches may be used to help maintain patient privacy in a system like that described above. For example, a tracking system may simply be provided with transponder ID's for tracking of patients, but may not be provided with any information by which to associate a particular patient with a particular transponder. In addition, a tracking system may be controlled to authenticate requesters for tracking information, and may only give access to trusted requesters, or may provide access on an as-needed basis. For example, a requester may provide information to a tracking system regarding a particular procedure, and the tracking system may then obtain information about the procedure from another portion of a system to determine when the procedure occurred, and to thereby limit the provision of tracking data about a patient to a particular time period around the time of the procedure, and may provide information only for locations of the patient that might be relevant to the particular procedure. Such filtering of time-location information may also occur in other parts of the system and for purposes other than patient privacy.

FIG. 1B is a conceptual diagram showing tracking of a home healthcare worker using a mobile computing device. In general, by techniques similar to those described above, the provision of healthcare outside a clinical setting may be tracked accurately and conveniently. In particular, a home healthcare worker 128 shown in a patient home 122 in this example, has been provided with a mobile device 126. The device may be a mobile telephone or smartphone, and may be a device originally owned by the worker 128 and supplemented with programs to permit the tracking described here, or may be a device given to the worker 128, such as by the worker's employer, specifically for the purpose of tracking services provided by the worker 128.

In this example, the worker 128 is tasked with providing home healthcare services to the resident of home 122, which is within a large city. Various other facilities may also be located within the city, such as a restaurant 134 and department store 132. The home healthcare worker is not supposed to spend time at either the restaurant 134 or the department store 132 when they are to be caring for the patient. Also, a cellular telephone tower 130 is shown to permit wireless communication with the mobile device 126. As described here, the device 126 may be used to verify that the worker 128 has worked with the patient, and how long they have done so.

In an example process, the patient may initially be enrolled with a system 120. Such enrollment may involve identifying an address for the patient's residence, along with a schedule for care of the patient. One or more caregivers may then be assigned to provide care for the patient, and may be assigned appointments during which they are to care for the patient. A scheduling system at a main server system may then interface with a scheduling system on the mobile device 126 so that appointments may automatically be added to the device 126, along with addresses or locations for the appointments. The worker 128 may thus start their workday by looking at the first appointment in their schedule and their device 126 may generate a map showing the location of the appointment (which information may have been automatically downloaded to the device 126 very early in the morning), by using address information in the appointment data. The worker 128 may then drive to the appointment, such as at home 122.

When the worker 128 arrives at the home 122, they may signal a start to tracking of their location. For example, they may select the appointment in their schedule, and a program, which may be a plug in program that interacts with a personal information manager (PIM) on the device 126, may begin running. The program may periodically record the location of the device 126, such as using known tower triangulation (e.g., GOOGLE MYLOCATION) or GPS techniques, such as every several minutes until the worker 128 terminates the program or the sensed location moves away from the home 122 (e.g., the worker 128 leaves). Such recording of location information may be stored as a time-location pair or in another manner, and may be stored at the device 126 or may be immediately relayed to a central location. For example, the device 126 may store all of the time-location entries for an entire day, and may only report back at a single transmission during the nighttime. Also, not all of the information that the device 126 collects needs to be reported. For example, in certain implementations, if the collected location information showed a relatively constant location over 12 readings taken every 5 minutes between 1 p.m. and 2 p.m., the device 126 might report back a single reading indicating that the device was at the general location that entire period, rather than reporting all twelve readings.

In addition, mechanisms may be provided to ensure that the worker 128 is actually at the location, so as to discourage dishonest behavior such as leaving the device 126 at a location and running errands while the worker is supposed to be caring for a patient. Such a sojourn can be avoided by programming the time-tracking application on the device to cause the device to beep periodically, and to thereby require the user to press a button on the device to indicate that they are still nearby.

In addition, a fingerprint reader or other biometric unit (such as a camera) on the device may be used to ensure that the worker 128 has not had another person interact with the device. For example, the worker 128 may be asked to take a picture of themselves, and the photo may be uploaded to a central server so that system administrators may at that time, or at a later time, verify that the actual worker was at the location (and did not, for example, pay someone less money than they were making to sit in for them). In certain implementations, the patient may also be prompted for biometric input or prompted to provide a password when the treatment session has ended, so as to indicate that they were at the appointment and that treatment was provided satisfactorily.

When the worker 128 has completed the appointment, they may indicate such completion to the application, such as by selecting an icon that has been visually displayed on the device 126. Such an action may simply stop the clock from running, or may result in other actions occurring, such as in the device 126 reporting to a central server that the appointment has been completed, and receiving back from the central server new instructions for the worker 128.

The worker 128 may then look at their scheduling application to identify the next client location to which they are to travel. The worker 128 may then repeat the process of arriving at a patient location and activating time tracking on their device 126. Such actions may be repeated throughout a workday. Also, in certain implementations, motion of the worker 128 when in transit may also be monitored, particularly if the worker 128 is compensated for such commuting time. Likewise, motion may be tracked to ensure that the worker is following an appropriate route and is not speeding, in much the manner that long haul truckers have traditionally been tracked with dedicated tracking units.

The mobile device 126 may be a general programmable device, and may be conveniently programmed to provide such functionality as that just described. The device 126 may, for example, run off of an operating system such as the ANDROID operating system, WINDOWS MOBILE, SYMBIAN, APPLE OS X (for the IPHONE), or other such operating systems. The device may have calendaring and GPS location tracking capabilities built in, and the program for tracking time-based activities by a caregiver may make use of such built in services. As a result, in a basic form, the program need merely accept inputs from a user and record time-location entries when each input occurs (and then provide such data to a properly authenticated requesting server). In more complex implementations, the program may call for entry by a user periodically when the program is running, and may record time-location information when such inputs are obtained. In a yet more complex implementation, the program may be fully integrated with calendar and mapping applications so that the user may call up an appointment, be provided with directions to the appointment, and report back timing and location information to a central service, where such information is automatically correlated to the identity of a patient at the location of the appointment.

Certain of such services may be accessed from a remote server, such as by using asynchronous Java and XML (AJAX) programming techniques. For example, an address may be parsed from an appointment, and the address information may be provided, via a standard API, to an application such as GOOGLE MAPS. The personal information manager may also be a hosted application, and may be accessed by a web browser or similar application running on the device 126. Other various services and data may be stored on the device 126 or accessed from a central server, as the need is presented by a particular implementation.

Although tracking has been described here as occurring with a handheld mobile device 126 like a smartphone, the tracking may alternatively or in addition be conducted by another form of device such as a device in the worker's automobile 124. For example, certain devices such as the SAT100 from Procon, Inc. (Knoxville, Tenn.) or the ZoomBak Car Locator from ZoomBak LLC (New York, N.Y.), can track worker locations. Devices of this type may be mounted inside an automobile and powered from the automobile, such as from a lighter outlet. The devices may report their locations to a central service using on-board GPS capabilities, either when activated by a user, when called from a central system, or at periodic intervals.

On the server side of the system 120, and as described in more detail below, the time-location data provided by device 126 may be compared and resolved with patient and schedule data. For example, a server may step through a worker's 128 schedule data that is stored on the central system (and that may be synchronized with the user's device 126). Each appointment in the schedule may be associated with a particular patient. The server system may use the patient data to identify a location for the patient, which may be a plain language address or may alternatively be a lat/long pair or the like. Where the information is in the form of an address, it can be converted into a lat/long pair. The location information and the time for the appointment may then be resolved against time-location information received from device 126 to determine whether the worker 128 spent a sufficient amount of time with the patient, and whether such time was near to the scheduled time for the appointment. If the worker 128 did spend the time at the particular location, the system may infer that the scheduled care was given, and may bill the patient (or their payor) and pay the worker 128 or otherwise give the worker credit for providing the care.

Certain rules may be applied by the system to ensure that matches are made when appropriate and are rejected when appropriate. For example, a location of a worker may be considered to be a match when it is within a set distance of a centerpoint for a patient's home, or within a peripheral boundary for the patient's home, which would be sized to compensate for error and uncertainty in GPS or other readings, and for various parking problems (e.g., if the worker must park down the street) where the device is mounted in an automobile. In a like manner, recorded times for care may be "softened" so as to make a match more likely, so that, for example, a worker will be determined to have given proper care if their arrival and departure were within 10 minutes of the scheduled arrival and departure times.

Also, where a worker is running early or late, they may be given the opportunity to move an appointment forward or backward in their schedule, which may cause the rest of the appointments in their day to slide appropriately, or for one or more appointments to be assigned automatically to another worker. In such a situation, a message may also be sent by a system automatically, e.g., by automatic telephone dialing, e-mail, or text message, to any patients who will be affected by the change in schedule.

The worker may also be given the opportunity to turn off any tracking, and the device may be made to clearly notify the worker when tracking is occurring. For example, the program that seeks input from the user may be the default program shown on a display on the device 126 when it is active so that it cannot be minimized or otherwise hidden from the user. Likewise, whenever the program is removed from view of the user, it can be blocked from recording location information. In such manners, the worker may be ensured that they will know when time-location data is being stored or recorded, and can know that they can turn off such a function easily and securely at the end of a workday.

Additional tracking functionality may also be provided for the mobile device 126. For example, the device 126 may include a panic button that a user may press or otherwise activate so as to cause a central tracking organization to attempt to contact the user, and then to send emergency personnel to the location of the user. Thus, for example, if a homebound patient has severe health problems, a caregiver can readily get them help, or if the caregiver is in trouble, they may get help for themselves. The location of the caregiver may also be used to identify the particular patient, and the patient's medical records may be downloaded automatically to emergency personnel so that they can be knowledgeable when they arrive at the scene. In addition, similar functionality may be provided by a key fob that the caregiver may carry, and that may communicate, for example, to the caregiver's mobile device 126, whether hand-carried or in the user's automobile.

Other specialized applications may also be provided on the mobile device 126, and may be integrated with the systems and features just discussed. For example, an application for downloading and reviewing patient information in a secure manner (i.e., to protect patient privacy) may be provided, and may have the appropriate patient information selected by comparing a location in a user's daily schedule, or the user's current location, to a database of patient addresses. The user can have records presented as images or as actual electronic records, and may thereby enter data about the patient quickly and in a manner that it is immediately uploaded and stored at a central records server, without the user to do anything more. Access to such information may be limited only to users who will be treating a particular patient, and only for a time period necessary to give the patient such treatment.

Additional tracking and reporting may be conducted by a central system. For example, start-stop reporting may be provided, where a service registers each location at which a worker stopped for a sufficient predetermined time period (e.g., more than a typical stop-light delay). Such information may be used, along with a history of start-stop data for a worker, to verify locations at which the worker stopped (or did not stop, such as at a patient's house), and may be compared against geo-data such as store names, so as to determine that a worker frequently stopped at a particular store (e.g. a coffee shop). The information may depend entirely on GPS or other location data, or may also determine a "state" of the user's automobile (e.g., park, drive, etc.) when the user stopped, so as to better infer the actions a user is performing. Such information may also be used to generate forms of "idle" reports, which will reflect how much time a user idles or sits in one location, particularly with the engine running. The information may be used to help make various mobile workers more efficient and to provide them with additional tools they may need in order to be efficient. In addition, similar information may be used to deter behavior that may increase insurance costs, such as speeding—in manners already familiar in other industries like trucking, as noted above.

Moreover, such data can be used to determine a total number of miles traveled by a worker during a shift, so as to permit automatic mileage reimbursement for the worker. Such a feature may save the worker from having to fill out tedious paperwork, and can save the employer from having to process the paperwork. Also, it lowers the risk of fraud or errors in transcribing mileage to a reimbursement form. Moreover, the data may be used in a manner like LoJack, to help recover a stolen vehicle by reporting in location information for the device.

In this manner, actual care provided by a worker—in this example a healthcare provider—may be tracked to ensure that appropriate work is being carried out. Such tracking may occur using standard hardware such as that discussed above, including a smart phone that a worker may already own and that they may already be comfortable using. The additional capabilities may be provided by adding a software module to such a smart phone, or by accessing a hosted application such as by using a Web browser on a mobile device. The time and location data may be transferred conveniently to a central server where may be analyze such as the matters discussed below. As a result, time and location data that is accurate may be gathered conveniently, without the need for substantial capital investment, and without the need for time-consuming training of personnel, in certain implementations.

Figure 2A:
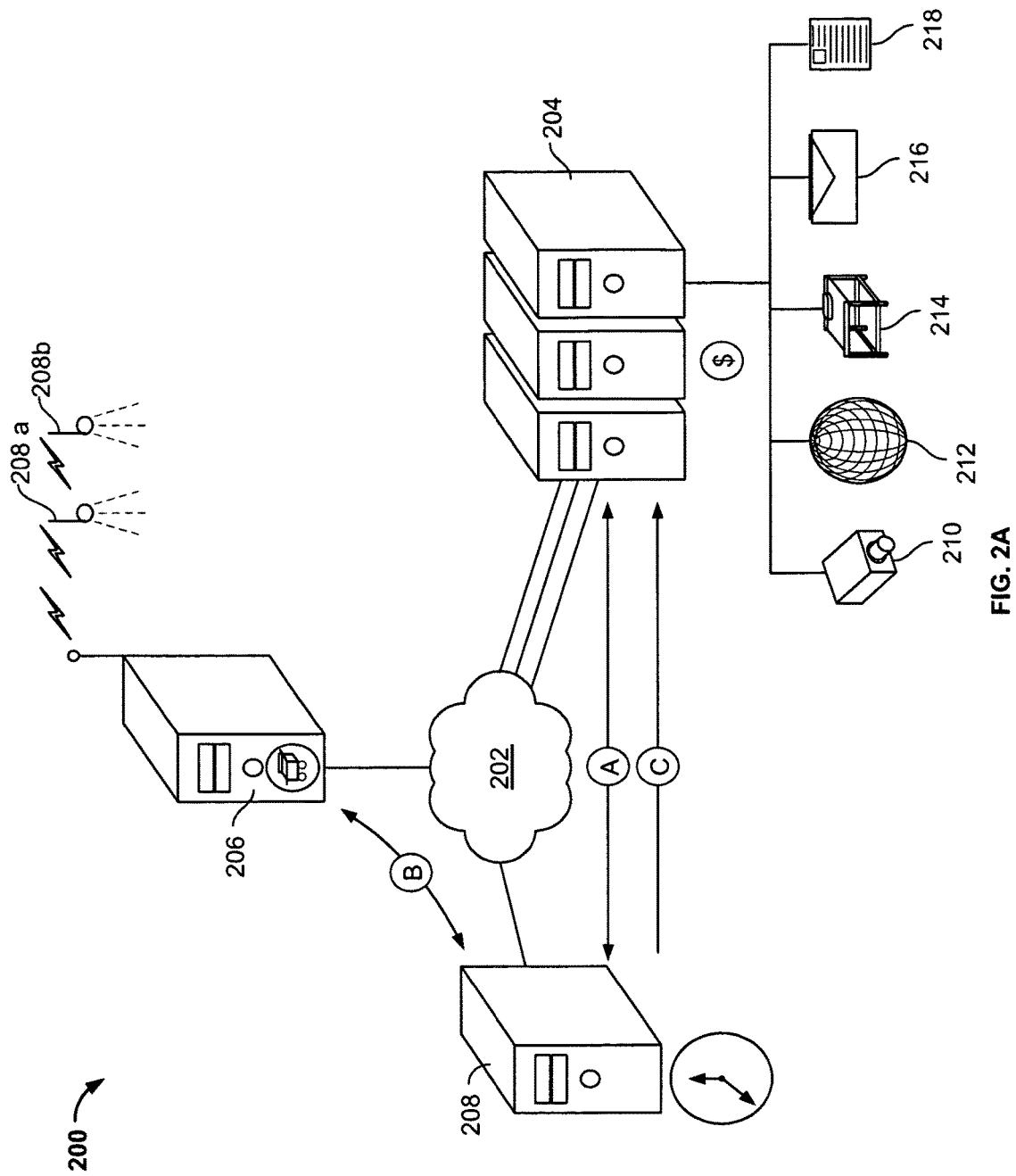
FIG. 2A is a schematic diagram showing a system for tracking patient activity.

FIG. 2A is a schematic diagram showing a system 200 for tracking patient activity. In general, the system 200 provides a number of structural components for correlating time and location data for objects in a health care facility, with a billing system associated with the facility. The system 200 generally includes a number of servers connected by a network 202, such as a local area network or a wide area network. The servers include a group of billing servers 204 running a patient billing system, a location server 206 that tracks locations of objects in a facility or facilities, and a patient tracking server 208. Though expressed and shown as separate servers, the particular servers may be combined into one or more common servers, or actions provided by a particular server may be shifted to another server or other servers.

In certain implementations, the system 200 may be implemented in a modular manner so as to permit existing systems to be integrated with each other or to permit new functionality to be added easily to existing systems, so as to provide the functionality described in this document. For example, billing servers 204 may run and operate standard billing systems from a variety of vendors, and may be communicated with through an application programming interface (API) in familiar manners. Likewise, the location server 206 may be able to operate software from various vendors for tracking locations of objects, such as objects equipped with RFID tags. Communications with the location server 206 may occur via queries or other form of API. Time-location billing capabilities may then be provided as an add-on feature to such systems, such as part of a plug-in module, or an additional server that monitors the operation of the main servers and receives periodic calls from the main servers and provides information in response.

Billing servers 204 may provide for various functions relating to the operation of a healthcare organization. For example, billing servers 204 may track the admission, treatment, and discharge of patients, along with tracking procedures and other activities related to the patients. In doing so, billing servers 204 may create bills or invoices for payments relating to patients, and may provide the bills to the patients, insurance companies, or the government, as appropriate. For illustrative purposes, billing servers 204 are shown as larger and greater in number than the other components of system 200, to reflect that billing and scheduling systems in a healthcare organization are generally large and complex. However, the arrangement of the particular components here is not meant to be limiting, and various numbers, arrangements, and types of computers may be used in the system 200.

Various ancillary billing functions may also be provided by the billing servers 204. For example, dispute resolution module 210 may be provided to track disputes over bills or disputes over billing (e.g., when patients or caregivers dispute their payments). Report module 214, pictured as a printer, may produce various reports (electronically or on paper) relating to patient care, billing, financial performance, and other such reports typically generated by a healthcare information system. A bill distribution module 216 may provide for the aggregation of billed items into a bill, whether electronic or on paper, and for the distribution of such items to the appropriate payor, such as insurance companies and/or patients. Bill creation module 218 may generally provide for the assembly of bills which may subsequently be distributed by bill distribution module 216 or by other mechanisms.

Billing servers 204 or other similar systems within system 200 may provide additional functionality. For example, system 200 may be provided with electronic medical record functionality, whereby patient charts and other similar information are stored electronically, and are accessible without a need for paper records. In such an implementation, the portion of system 200 responsible for the electronic medical records may provide information such as information about procedures performed on the patient, to other components in system 200 (with appropriate security). With respect to tracking procedures performed on a patient, entries in an electronic medical record may be used to establish or verify the timing of certain events in a patient's care. As one example, it may be possible that a facility prevents a certain event, such as a surgical procedure, from being performed until a nurse or physician has entered a particular value into a medical record. Thus, if billing for the procedure occurs before such a value is entered, it may be presumed that there is an inaccuracy in the medical record or in the billing records.

Location server 206 generally includes components for receiving signals from sensors 208a, 208b, and for storing information associated with the events that triggered the signals. For example, the location of each sensor 208a, 208b may be registered with location server 206, and identifiers for objects that fall within the spatial range of the sensors may be transmitted to location server 206. For example, an RFID chip may transmit a unique digital code representative of an identification number for an object to which the RFID chip is attached. That unique code may be forwarded from the sensors to the location server 206, and the location server 206 may generate a timestamp for the event of the object falling within the range of one of the sensors. From this received and determined information, the location server 206 may provide information about the identity of an object, its location at certain times, and the times when the object was in each particular location. Sensors may themselves timestamp certain occurrences and may also store the occurrences and submit them to a central system using batch processing.

Patient tracking server 208 may communicate with location server 206 and billing servers 204 to provide for tracking of patients for the purpose of producing or verifying billed amounts for patient care. Although shown as a separate server, patient tracking server 208 may be provided as part of location server 206 or billing servers 204 (and all of the components may be provided on one single server or group of servers). For example, the functionality of patient tracking server 208 may be incorporated as a plug-in or other similar module that may be added to a pre-existing patient billing system. In a similar manner, such functionality may be incorporated directly into a base patient billing system.

Lettered arrows in FIG. 2A provide an example of communications that may occur during a process for establishing or verifying billing for a particular patient. Arrow A shows initial communications between billing servers 204 and patient tracking server 208. For example, billing servers 204 may be involved in a patient billing cycle, such as a monthly billing cycle.

Appropriate events for which billing is to occur may first be determined. For example, in preparing bills for the monthly billing cycle, portions of the patient billing system may recognize the presence of a procedure performed on the patient (e.g., by the occurrence of a billing code for the procedure in the patient's records) that corresponds to implemented patient tracking technology in the system. As one example, the procedure may be flagged as a procedure that involves time-based billing by one or more caregivers. Upon recognizing such a procedure, the billing servers 204 may submit a request to patient tracking server 208, where the request includes an identity of the relevant patient, an identity of the relevant caregiver, and an approximate time for the procedure. Using the received information, the patient tracking server 208 may query the location server 206, as shown by Arrow B, to obtain data for all stored triggering events for the relevant patient and the relevant caregiver around the identified time. The location server 206 may return such information, and the patient tracking server 208 may filter the information to identify which of the triggering events are also billing-related events.

In the example discussed above, the billing-related events may relate to times at which a caregiver first sees a patient or a time when a patient leaves a pre-op area, and a time when the patient returns to a recovery room. According to an agreed-upon protocol, the patient tracking server 208 may return relevant information to the billing servers 204, such as starting and ending times for the particular caregiver for the relevant procedure, or a computation of the amount of time allowed for the caregiver with respect to the procedure (Arrow C). The billing servers 204 may then compute a billed amount using such information, or may compare the computed amount to a reported amount obtained by other mechanisms (e.g., based on time information written down by the caregiver). When comparing such amounts, the system 200 may generate an exception where there is not a close enough match, and may employ various mechanisms for resolving the exception, as discussed in more detail below.

Figure 2B:
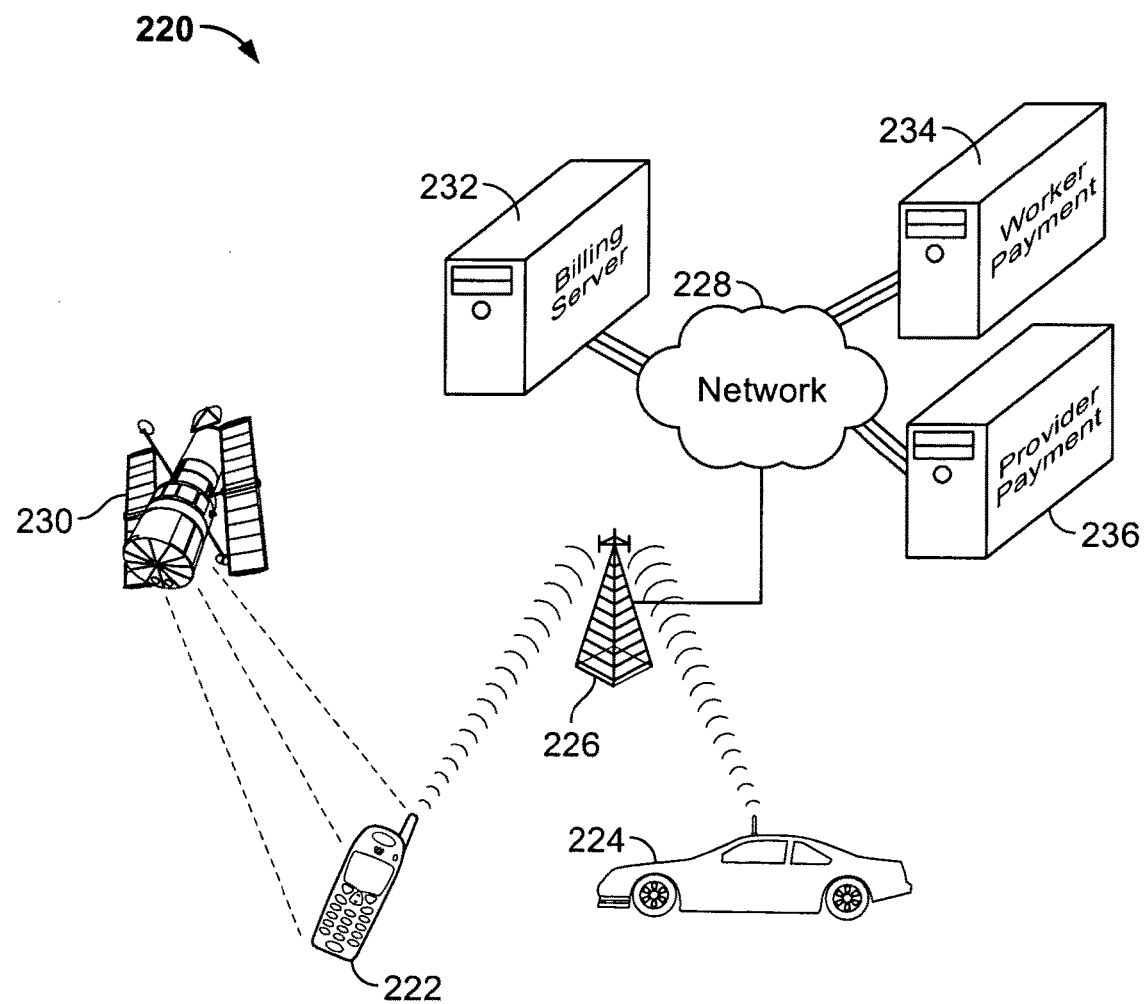
FIG. 2B is a schematic diagram showing a system for tracking caregiver activity.

FIG. 2B is a schematic diagram showing a system 220 for tracking caregiver activity. The system 220 may be similar to that shown in FIG. 1B. In this example, the system 220 is shown as involving mobile devices such as a portable mobile device 222, in the form of a smart phone, or an automotive mobile device 224, such as a vehicle navigation system or vehicle tracking system (e.g., an electronic device that plugs into a lighter of an automobile and reports its location to a central service). Devices 224, 222 may determine their geographic locations using GPS data obtained from a plurality of orbiting satellites 230, or from tower triangulation techniques, in various known manners. The devices 222, 224 may further provide information about their locations and other information through a wireless network 226 and then through network 228, such as the internet. Communications through the network 226, 228 may be encrypted or otherwise made safe from snooping by third parties.

The devices 222, 224 may collect time and location data in accordance with healthcare services that are to be provided by a user of the devices 222, 224, and may return data back to a central system that is shown in this example by a number of servers. A billing server 232 maintains records for patient care for a healthcare system and makes determinations regarding when such care has been provided, and whether patients are to be billed for the care. In addition, the billing server 232 may be supplemented with program modules that accept time and location data from mobile devices to determine when patient care has been provided.

For example, billing server 232 may store data about patients in a system, along with information about the location at which those patients are to be treated (e.g., their homes). The billing server 232 or a related server or service may generate schedules for patient care and may associate particular patients with particular caregivers. Periodically, the billing server 232 may transmit such schedules to various workers, such as at the beginning of a work day or the end of each day for scheduled work the following day. The schedule information may be transmitted in an agreed-upon format, so that scheduling applications, such as OUT-LOOK MOBILE or GMAIL may present the information in appropriate manners to various users.

The billing server 232 may in turn receive time and location data from the devices 222, 224, and may resolve that received information against the schedule information. As one example, the billing server 232 may receive numerous periodic signals from a particular device, and may convert the data for those signals into a reduced form, such as by identifying, from numerous data points, a much smaller number of locations at which the caregiver stopped, and identifying time ranges over which the caregiver stayed at those locations. In such a manner, a schedule for the caregiver's actual operations may be created, and may be compared by the billing server 232 to the planned or assigned schedule for the caregiver so as to determine whether the caregiver succeeded in providing care to each patient in the plan.

Where the billing server 232 determines that appropriate care was provided, it may post a transaction for a particular care event with the system. Such a transaction may cause a line item to be added to a patient's bill to account for the care that was given. The billing server 232 may then report out such information to other components, such as a worker payment server 234. The worker payment server 234 may be programmed with payroll modules that are designed to ensure that workers in a system are paid properly. Where a caregiver has been found to have provided care for a particular patient, the billing server 232 may cause the worker payment server 234 to execute appropriate payment to the worker.

In a similar manner, the billing server 232 may request payment from provider payment server 236. The provider payment server 236 may be a payment server associated with a health plan, an insurer, or another payment entity within a health care system. Such a request for payment may be made by the billing server 232 using a mechanism such as electronic data interchange (EDI), and may include information such as an identifier for the patient account, a code for the care that was provided, and an amount of payment requested.

Using such a system 220, a healthcare provider may help ensure that patient billing and caregiver compensation more accurately reflect care that was actually provided to patients. Although shown as particular servers for clarity in FIG. 2B, the components of the system 220 may take a variety of forms, including by combining certain functionality into a single system or sub-system, or by splitting responsibility for certain functionality. For example, a billing server 232 may initially exist in a healthcare system and may not initially support location-based billing. Such a server 232 may be supplemented with software modules or with separate servers that may obtain information such as patient schedule information and worker location information, may determine whether the patient care occurred, and may provide data indicating the occurrence of such care to the existing billing server 232.

Figure 3A:
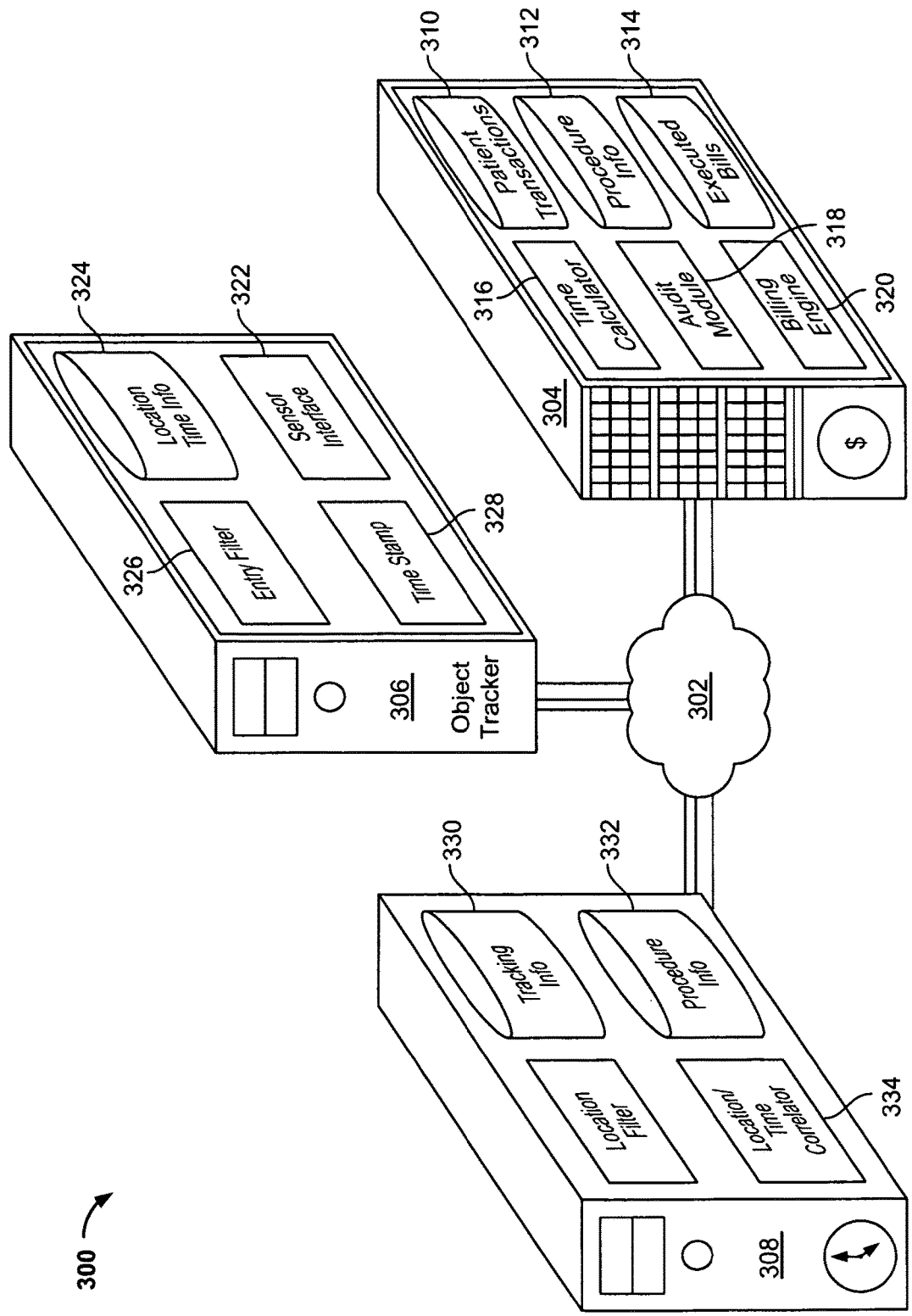
FIGS. 3A and 3B are schematic diagrams showing computing structures in healthcare billing systems.

FIG. 3A is a schematic diagram showing computing structures in a healthcare billing system 300. In general, the system 300 is arranged for illustrative purposes similar to the system 200 in FIG. 2A. However, particular arrangement of the components within the system, and the particular functions performed by such components may vary depending upon the particular implementation.

Here, the system 300 is shown as including a billing server 304 in the form of a rack or blade server, to indicate that such a server is typically relatively large and complex. The billing server 304 communicates through network 302 with an object tracker server 306 and a time/location server 308. Particular exemplary components are shown inside each of the servers 304, 306, 308.

Billing server 304 may include, for example, databases 310-314 relating to patients and the care and billing of patients. Patient transactions database 310 may track the various procedures performed on patients, and the various medications provided to patients. Such information may be used, for example, to generate bills relating to care for particular patients. Procedure information database 312 may include information relating to particular procedures performed on patients. For example, procedure information database 312 may include information relating to a fee schedule for particular procedures, the times when particular procedures were performed, the patients on which the procedures were performed, and the location or locations of the procedures. In this example, procedures may be broadly defined to include surgical procedures, dosing of medications, checking patient vital signs, and other such actions performed on or on behalf of a patient. Executed bills database 314 may include information for billing of patients, such as itemized billing information that may be provided by a patient or a payor associated with the patient.

Various modules within billing server 304 may access and analyze information such as the information stored in databases 310-314, may perform certain operations on such information, and may produce various reports or other output related to the information. For example, a supervisor may generate reports to better see the extent to which various workers are utilized so as to re-allocate workers to areas that are busiest.

Time calculator 316 may receive information relating to various procedure-related times, such as times at which a patient arrives in certain areas of a facility, or when a caregiver arrives in certain areas of the facility. Audit module 318 may contain code for operating a workflow to resolve exceptions found in data in system 300. For example, audit module 318 may provide for the review of information relating to patient billing in the comparison of different forms of data than they may provide input for patient billing. In particular, if time-location billing information does not match billing information manually entered by caregivers, the audit module 318 may manage a workflow for determining which entry method is likely the accurate method. The billing engine 320 may provide for traditional core healthcare billing functions, such as managing other modules to identify procedures performed on patients and other services provided to patients, and generating bills and follow-up materials related to such activity.

Object tracker 306 includes various components for receiving information about object locations (e.g., patient, caregiver, and equipment locations) in the facility, formatting such information, and storing the information for retrieval by various other services within system 300. Sensor interface 322 receives data from remote sensors, and may also provide information for controlling remote sensors. For example, sensor interface 322 may be communicatively connected to one or more wireless transceivers for receiving indications from sensors when transponders in a system pass the sensors. Timestamp 328 may be provided to associate a time with the triggering events sensed by sensor interface 322. For example, a triggering event may be provided with a unique identification number, and may be stored with an identifier for the transponder that was sensed, an identifier for the sensor (or a location of such a sensor, or other such information), and a time indicating when the information was provided to the object tracker server 306, as determined by timestamp 328.

Location/time information database 324 may store such location-time information (e.g., pairs of location data and triggering time data, along with other data such as object ID data), along with other information needed for the operation of object tracker server 306. Entry filter 326 may perform logical operations on data that is produced by triggering events before or after the data is stored in location/time information database 324. With respect to filtering before storage of triggering event information, entry filter 326 may be provided with rules to determine which triggering events generate data that may need to be accessed later, and which do not. For example, triggering events associated with patients, where the events do not correlate to the patient's room or to any other location associated with patient billing or other such tracked information, may be filtered by entry filter 326, and not be stored in location/time information database 324. Various other examples also exist regarding triggering events that may not require long-term storage.

Entry filter 326 may also filter information after it is stored, such as when a request for information is made by another server in system 300. For example, another server may request information relating to a particular procedure performed on a particular patient. Entry filter 326 may serve to query location/time information database 324 to obtain such information. In addition, entry filter 326 may limit the amount of responsive information that is returned to such a request. As one example, location/time information database 324 may store a number of triggering events relating to a patient in a particular procedure, but only a limited number of such events may be relevant to a query made by another server. In such a situation, rules associated with entry filter 326 may review the request, determine which portion of the located information is necessary to fulfill the request, and may filter out unnecessary information from any response.

Location/time server 308 may be provided to access information stored by object tracker database 306, process such information, and provide input to billing server 304 to assist in a patient billing process. Location/time server 308 may include a location filter 336 that may provide for further filtering of object tracking information received from object tracker server 306. For example, where entry filter 326 is not present, or where it only partially filters results, location filter 336 may provide additional filtering as directed by a query associated with location/time server 308. As indicated above, such various forms of filtering may be directed to lessening computing load on a system, to helping identify appropriate time information, and/or to improving patient privacy.

A location/time correlator 334 may be provided to perform certain operations on information received from object tracker server 306 relating to locations of patients or caregivers, and times at which the patients or caregivers were sensed as being in the particular locations. As one example, the location/time correlator 334 may fetch a pair of time entries from location filter 336 (e.g., an entering and exiting time for an operating room), by identifying an object and a location for the object, may filter out irrelevant entries where there are too many entries, and may perform an operation such as a comparison and subtraction on returned values to generate, for example, an elapsed time for a patient in a particular area of the facility. As with other modules discussed with respect to system 300, location/time correlator 334 may also be provided in a different server or in a different manner in system 300.

The components of location/time server 308 may access information stored locally, either temporarily or on a long-term basis, from databases on server 308, or may access remotely stored information. For example, procedure information (which may be obtained from billing server 304) may be stored in procedure information database 332, so that location/time server 308 may readily associate patients, locations, and caregivers with each other when queried for information by billing database 304.

Tracking information database 330 stores certain information obtained from object tracker server 306, or that is derived from such information. For example, location/time server 308 may periodically or continuously receive information about objects in a facility from object tracker server 306, and may retain only a subset of all such information that is relevant to its operations. For example, location/time server 308 may be concerned with the locations of patients and caregivers at certain points in time, but may be unconcerned about the location for other triggering events, and may also be unconcerned with the location of medical equipment (which may be tracked separately by an equipment inventory application).

Figure 3B:
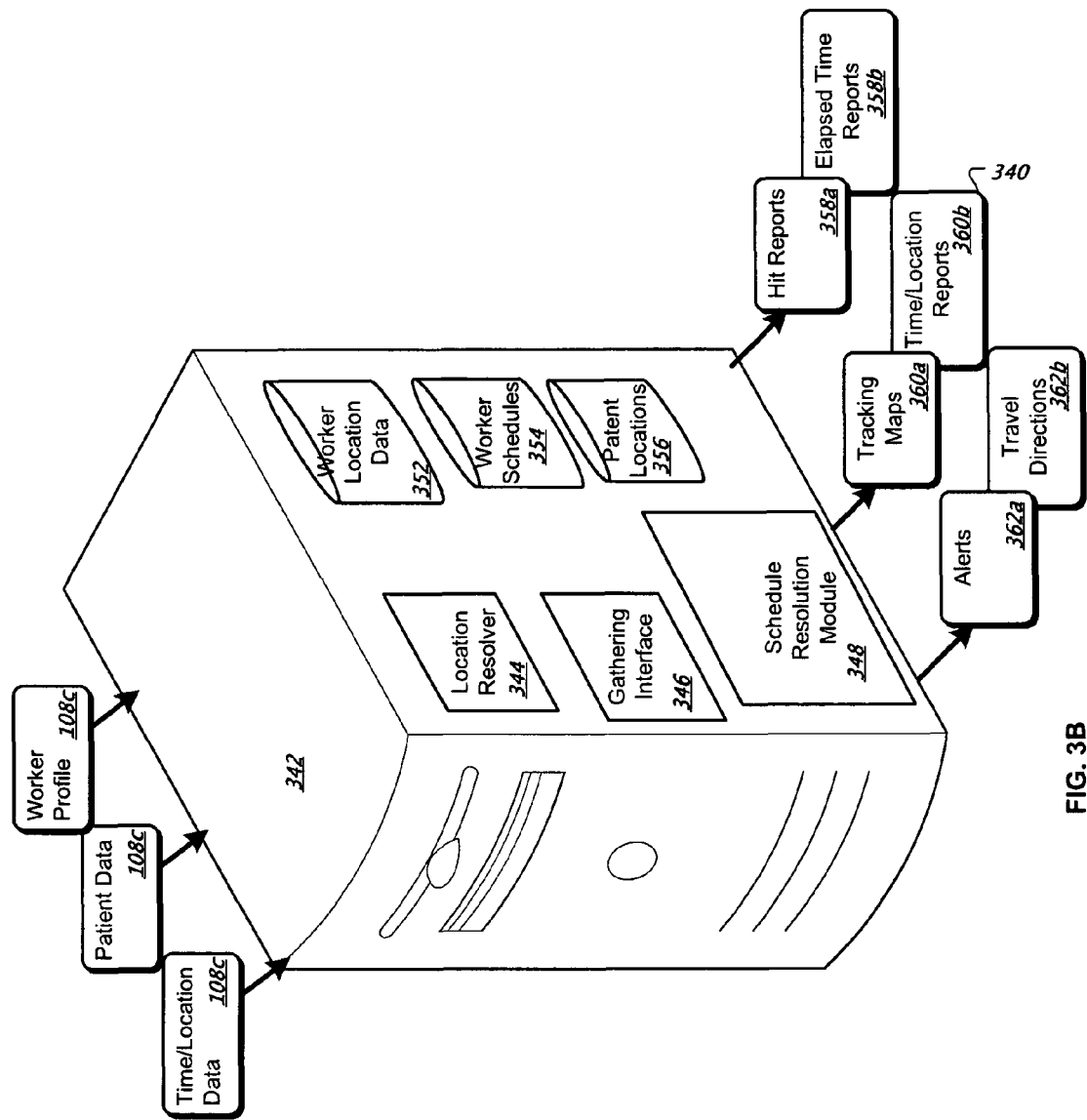

FIG. 3B is a schematic diagram showing computing structures in a healthcare billing system 340. In general, the system 340 may be used to carry out functionality like that described above for the system in FIG. 1B. For illustration, a number of components are shown with a server 342 for tracking time and location data for healthcare providers. The particular components are shown for illustration only, and other components may also be used in appropriate circumstances.

The server 342 may take a variety of inputs, including time/location data 364. Such data may include paired information for time and location of mobile devices associated with health care workers, such as latitude/longitude locations for devices, along with times at which the latitude/longitude information was recorded. The time/location data 364 may be received in real time, point by point, or in a batch mode. For example, mobile devices may take time/location readings throughout the course of the day, and may only report the information at the end of the day, so as to minimize communications with the server 342.

Patient data 366 may be provided to server 342 so that server 342 may determine whether a worker has provided care to a particular patient. The patient data 366 needed by the server 342 may simply include a patient identifier and information identifying a location for the patient's home. Additional information may include scheduling information reflecting when the patient is supposed to receive care from a caregiver.

Worker profile information 368 may include various information about health care workers that are to care for patients. For example, a worker profile may include a worker identifier along with information about a mobile device associated with the worker. Such information may include an IP address, a telephone number, and/or an e-mail address for the worker's device, and may also include information about the capabilities of the worker's device, so that server 342 may provide information to the device in an appropriate format and manner. For example, if the device uses only hosted services, the server 342 may provide information to the device in the form of webpages.

A number of components within server 342 operate upon the received information to provide for tracking of caregivers and generation of information for billing out of care to patients by the caregivers. A gathering interface 346 is configured to receive information from mobile devices operated by caregivers. The gathering interface 346 may, for example, be a portion of a web server program to receive time and location information submitted by mobile devices. In addition, the gathering interface 346 may be programmed to request such information, such as at periodic intervals, as discussed above and below.

The gathering interface 346 may parse such information, including to identify location-related information provided by mobile devices. Such location-related information may be provided to location resolver 344. Location revolver 344 may convert received location-related information into a form that is more usable by the system 340. For example, the gathering interface 346 may receive particular latitude and longitude information from a mobile device, and the location revolver 344 may match such information to a location that is already associated in the system 340, such as a location of a patient home. In this manner, the location resolver 344 may be used to determine whether a reported location is a match for a location stored in the system 340. A mapping module 350 may be used to provide a graphical representation of a geographical area for a user. For example, address information for a patient may be provided to the mapping module, which may parse the address information and convert it for submission to a form that is usable by a map generator, such as GOOGLE MAPS. The mapping module 350 may then return one or more map tiles for display to a user, such as a user attempting to locate the patient household. Driving directions may also be provided to the worker in a familiar manner, and may take into account current traffic conditions (e.g., so that the worker can quickly move from one patient's home to another).

A schedule resolution module 348 may be used to resolve the time and location information received from mobile devices, with schedule information for patients and caregivers. For example, when location resolver 344 has identified particular locations for a caregiver, the schedule resolution module 348 may compare such locations to patient locations, and may further compare the time period during which the caregiver was at the particular patient location with a schedule setting forth the locations at which the caregiver was supposed to be present. The schedule resolution module 348 may then provide an indicator of the total elapsed time that the caregiver spent at the particular location, and in certain implementations, may provide an indicator of a pass or fail for the performance of the care by the caregiver.

The components of server 342 may access a variety of stored data in performing the described operations. For example, a worker location data store 352 may contain time and location information reported by various workers in a system. Such information may be stored as time and location pairs in lists under each individual worker that is registered with the system 340. The data may also be stored in other convenient manners in appropriate circumstances.

Worker schedules data store 354 may store schedule information for various workers in the system 340. Such schedules may include references to particular patients who are to be treated by the workers as part of the schedules. Patient locations data store 356 may include information describing locations at which particular patients are to receive care by the caregivers. Such information may be compared to information in the worker location data store 352 to confirm whether particular workers arrived and stayed at the patient locations for a sufficient period of time.

Server 342 may, in this example, produce a variety of output information. For example various reports 358a, 358b, may be produced by the server 342 and may be used by other components in a larger system. As one example, hit reports 358a may indicate situations in which there has been a match between a worker's scheduled duties and actual location of the worker during a work day. The hit reports 358a may represent situations in which the worker was at an expected location, so that the reports indicate success and good work. In a similar manner, "miss" reports may be generated for a supervisor to quickly see where there may be developing problems.

Elapsed time reports 358b may provide additional detail that indicates the amount of time that the caregivers spent at an appropriate location. The elapsed time reports 358b may be used, for example, by a healthcare billing system to determine the amount that a patient is to be billed for a particular episode of care, and an amount that a worker is to be credited for providing such care.

Information about worker locations may also be provided. For example, tracking map 360a may show particular locations of a caregiver during the day. The tracking map, for example, may show a path followed by a worker during the d, with the speed of the worker during those periods. For example, a number of dots in one small area may indicate that the area was a home for a patient of a healthcare worker, while more distantly spaced dots may indicate a commute by the worker between the homes of two different patients. The tracking map 360a may thus be used to better understand the progress of a worker throughout a day, and may also be used to help identify more efficient patient assignments for workers so as to minimize the distance that workers have to travel during the workday. Time location reports 360b may simply provide raw time and location data from various remote devices, or may provide similar process data, such as data that summarizes multiple time/location reporting from a device into a single identified arrival, with the caregiver staying for a certain period of time.

Alerts data 362a may take a variety of forms. For example, an employer may wish to provide alerts to one or more caregivers in a system, such as to indicate that a schedule has changed (e.g., by a patient not being able to make an appointment), or other similar information. Alerts may also be provided to patients, such as indicating that their caregiver will be slightly late, by calling the patients with an automatic dialing and voice generating system that plays a determined message for the patient. A system may use known contact information about workers and patients to generate such alert automatically without a need for tedious dialing and/or e-mailing by a supervisor.

Travel directions 362b may also be provided, as mentioned above, such as by identifying a current location of a worker compared to a location of a next appointment in the workers schedule. The travel directions may provide the worker with a convenient mechanism by which to reach a next patient location, without a need for the worker to identify and then enter information about the patient location.

Routing information for a worker may also be generated in real time or near real time using such a system, so as to best balance a system's capacity with the immediate load on the system. For example, as a worker leaves one house, they can indicate such activity using their device so as to cause a central server to find a next patient for them and to automatically download information on the patient (e.g., a map with suggested route, and limited medical records information) and the worker may go to the house of that patient. Using such a feature, a system may better manage employee capacity and ensure that each worker will have patients to see even if some patients cancel their appointments.

Figure 4A:
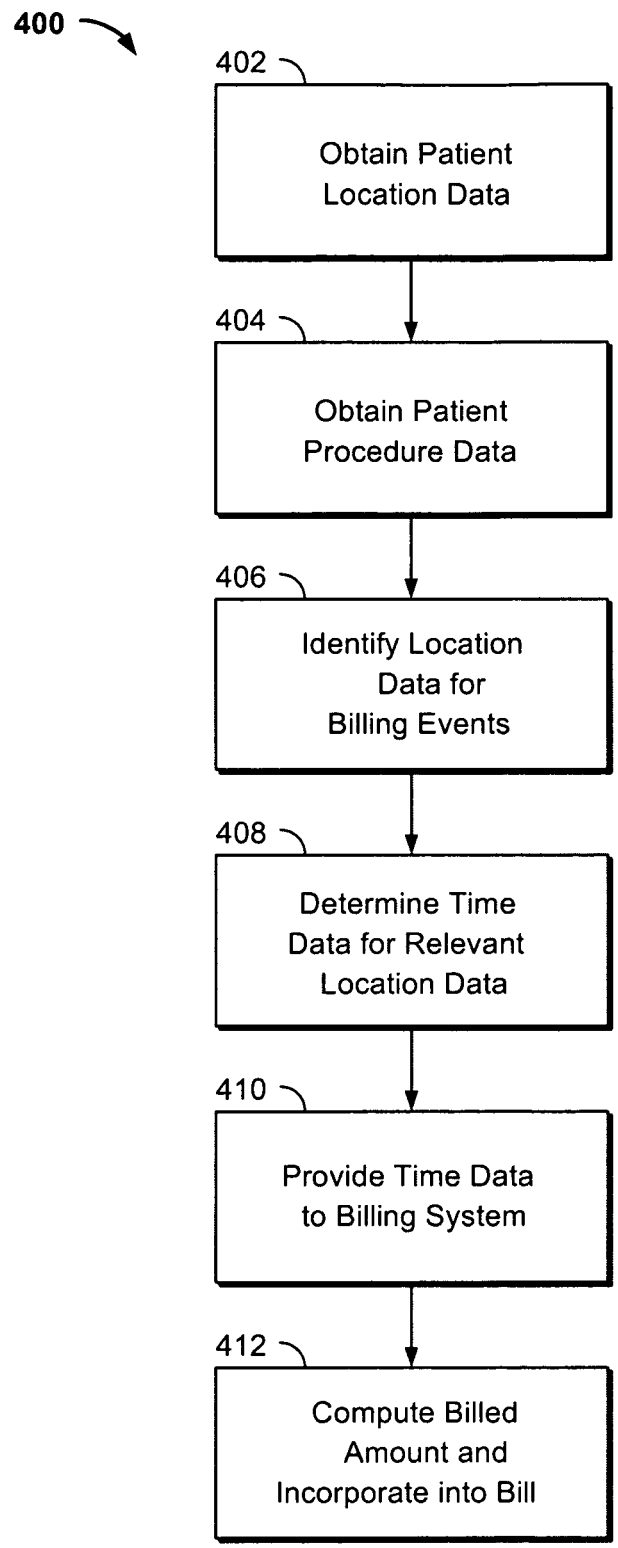
FIG. 4A is a flow chart showing actions associating patient activity with billing activity.

FIG. 4A is a flow chart showing actions associating patient activity with billing activity. In general, a process 400 is shown by which location data for patients and other objects in a healthcare facility may be tracked, and may be used to create or verify certain billing-related events. At box 402, patient location data is obtained for a healthcare facility. Such collection of data may occur continuously, as location sensors are triggered by the passing of various objects in the facility that been provided with transponders, such as RFID tags. The location data may be stored in various formats, including with time data associated with the times when certain locations were observed for the objects, and also with identification data for the particular objects. The storage of time information may take the form, for example, of Coordinated Universal Time (UTC). Storage of time data in a manner that does not depend on a particular time zone may be used, in particular, for an organization having facilities spread across multiple time zones.

At box 404, patient procedure data is obtained. The triggering event for obtaining such data may be the occurrence of a billing cycle, whereby a healthcare billing system seeks to obtain certain information for determining an amount to bill a patient. Such a system may send requests for information on procedures performed on the patient so that additional information regarding the procedures may be obtained before a billing action is carried out. For example, a database may be searched for all billing codes that have been entered during a particular period for that patient.

At box 406, location data for particular billing events is identified. For example, a procedure identifier may be provided by a billing system, and that identifier may be used to identify rooms associated with the procedure, and caregivers associated with the procedure. The locations of the patient and the caregivers at particular times around an identified time for the procedure (as obtained from a patient scheduling system) may then be retrieved, and may be filtered to identify location data that may be relevant for billing.

The system may then, at box 408, determine time data for relevant location data. For example, if arrival at a patient room by a caregiver is determined to be relevant location data and is filtered from a larger data set, the system may then perform a lookup to identify a time at which the caregiver arrived at the patient's room. In certain implementations, different times may be compared so as, for example, to compute an elapsed time, such as when the elapsed time may be multiplied by a billing rate to produced a billed amount.

With timing information determined, such information may be provided back to a more general billing system, as shown in box 410. The information returned may depend, for example, on the form of request from the billing system, and may be formatted according to an agreed-upon protocol. For example, the billing system may be provided with an identification number for a procedure, along with times that may be relevant to the procedure.

The billing system may then use the received times to compute a billed amount and incorporate that amount into a bill for the patient, as shown at box 412. For example, the billing system may compute an elapsed time for a billing event, using times received from another system, or, for example, a mixture of times entered by a caregiver and times measured by the system. As one example, a start time may be obtained from a medical record system, according to a time at which a particular entry was made on a patient's medical chart. An end time, in contrast, may be obtained from a patient location tracking system, such as the time that the patient left an operating room, or entered a recovery room.

Figure 4B:
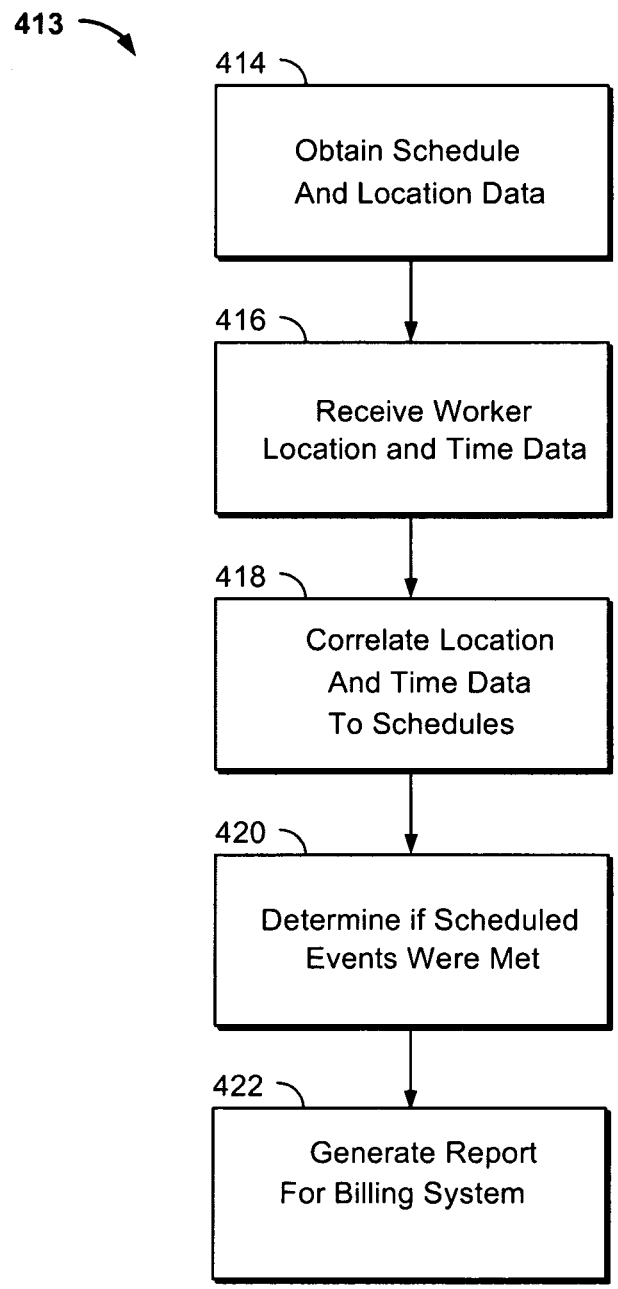
FIG. 4B is a flow chart showing actions associating caregiver activity with billing activity.

FIG. 4B is a flow chart showing actions associating caregiver activity with billing activity. Such a process may generally relate to care provided outside a healthcare facility, such as at-home patient care. The process 413 begins at box 414, where a system obtains schedule and location data for a worker. For example, such data may be obtained at the end of a workday or at the beginning of the day for the upcoming workday. The schedule information may include information identifying locations to which the worker is to travel for providing care, along with times at which the worker is to move from one location to another. The schedule information may also include location data that provides addresses or other location identifiers for patient locations. The information may appear to the worker in a manner much like meeting or appointment data in a standard application such as MICROSOFT OUTLOOK.

At box 416, the process 413 receives worker location and time data. Such information may be a simple pairing of a longitude and latitude for the worker, with a time at which a device for the worker measured the location data. Such data may be collected periodically and stored by a user device for later submission or may be submitted by the user device as it is collected.

At box 418, the process 413 correlates the location and time data to schedules for various workers. For example, the location and time data may be initially processed for a particular worker to identify a plurality of stops by the worker during a workday, along with a point for each of those stops, even where the worker may have moved around during the stops. The correlation may then involve initially identifying an appointment for the worker around the time of each stop, determining whether the observed location is sufficiently near the data for the patient location so as to infer that the caregiver was at the patient's house or other appropriate location, and then determining the amount of time that the caregiver spent at the patient's location.

At box 420, the process 413 determines whether the scheduled events were met or not. In particular, the process 413 may use the comparison between the scheduled events and the actual measured events to determine if the caregiver stuck to the schedule. Failures or failure signals may be generated in situations in which the caregiver never even arrived at a patient location, or did not stay long enough. Less severe failures may be indicated when a caregiver arrived at the location but their arrival did not match the schedule for the day, and the caregiver did not otherwise change the schedule in advance to indicate that they would not be on time.

At box 422, a report is generated by the process 413 to be provided to a billing system. The report may take a variety of forms, but may generally provide information that indicates whether and to what extent each caregiver provided services to patients, to a level that is needed by the billing system in order to provide accurate billing due to patients, and to provide payments to the caregivers.

Figure 5A:
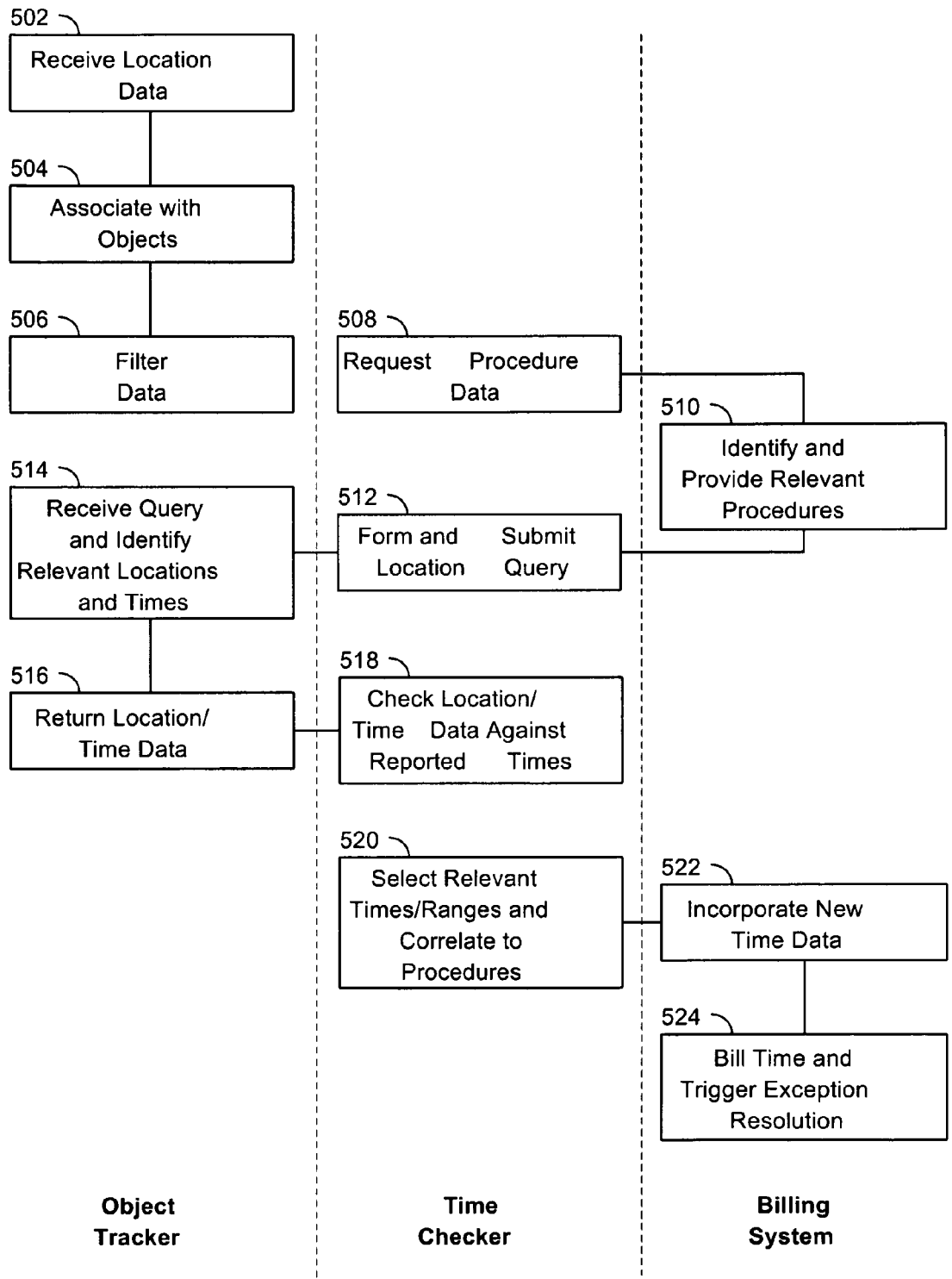
FIG. 5A is a swim lane diagram showing actions for coordinating patient tracking with billing.

FIG. 5A is a swim lane diagram showing actions for coordinating patient tracking with billing. In general, the actions here may be similar, in certain implementations, to the actions shown in FIG. 4A. The actions shown here are organized, however, for illustrative purposes, according to portions of a system in which they are performed. Those portions of the system are (a) an object tracker, which may function to receive indications of the locations of objects as they move through a healthcare facility; (b) a time checker which determines times or elapsed times of certain events in the system using information from the object tracker; and (c) a billing system, which may perform a variety of billing, patient management, and hospital management functions.

At box 502, location data is received by the object tracker, such as via wireless receivers that communicate with a central server. The received information may include ID numbers for particular RFID tags or other such transponders that are being interrogated. At box 504, particular objects are associated with the received data. For example, a table may include fields for RFID tag numbers and fields identifying particular objects (e.g., a patient wearing the particular tag on their wrist). The objects may include, for example, patients, caregivers, or movable equipment in a healthcare facility.

At box 506, the received data is filtered. For example, where the system serves multiple different functions, data for each of those functions may be broken out from other such data. As one example, tracking of patients may be separated from tracking of caregivers, which may in turn be separated from tracking of physical inventory such as equipment or medications. In general, the receipt of data associated with objects, and the filtering of the data, may be performed continuously as various objects are tracked as they move around a healthcare facility.

At some point in time, a time checker may request procedure data (box 508) from a billing system, or alternatively, a billing system may trigger itself to obtain such data. At box 510, the billing system identifies and provides relevant patient procedures associated with the request. For example, a request may seek all procedures associated with a particular patient and for a particular caregiver, and the billing system may return information regarding procedures for such a patient or caregiver. As one example, over a long hospital stay, one patient may have one or more operating room visits with attendant procedures performed on the patient, along with numerous physical therapy or occupational therapy sessions, before being released from the hospital. As shown in the pictured process, information about all such procedures, such as a location for the procedures, healthcare providers associated with the procedures, approximate time for the procedures, and other information, may be provided Time checker may then use such received information to form and submit a location query (box 512) to the object tracker. For example, the time checker may submit a query to receive all triggering events for a particular patient and for caregivers associated with the patient during a window of time around a procedure performed on the patient. As one example, if the procedure is identified as a physical therapy procedure, the billing system may check with a scheduling system to determine that the patient had a physical therapy session in the morning on a certain day, and the time checker may submit a query to the object tracker that would include all times in which the patient passed a sensor near a physical therapy department in a time window that covered that particular day.

At box 514, an object tracker receives a query and identifies relevant locations and times. In the example above, the relevant locations may be at a sensor near a door to a physical therapy department, and the times may be two times approximately 1 hour apart, when the patient passed through the doors. The object tracker may then, as shown in box 516, return such location and time data to the time checker. If three times are received for the sensor, so that clear entering and leaving times for a patient cannot be determined easily, various disambiguation rules may be used to determine which triggering events should be used to compute an elapsed time. At box 518, the time checker checks location-time data against reported times. In this example, the system is being used as a check on other reported times to ensure that those times were entered accurately and no errors were made. Thus, the time checker would access reported times, for example, entered by a physical therapist or anesthesiologist, for a procedure, as obtained from the billing system, and compare those times to the times measured by the system. Such a comparison, if an exception is generated, may be an indication that there was an error in recording time, and that certain follow up steps may be needed.

Figure 5B:
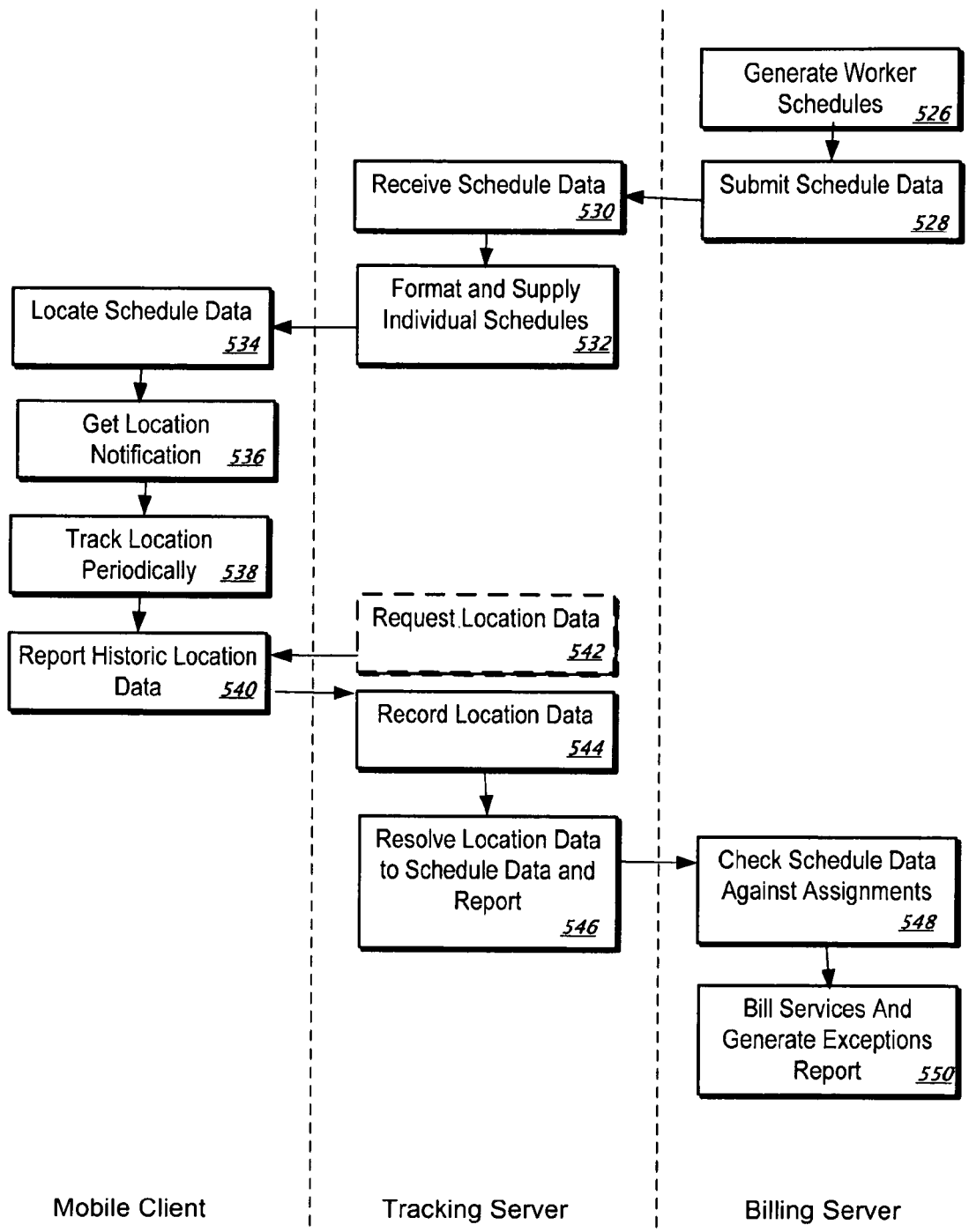
FIGS. 5B and 5C are swim lane diagrams showing actions for coordinating caregiver tracking with billing.
Figure 5C:
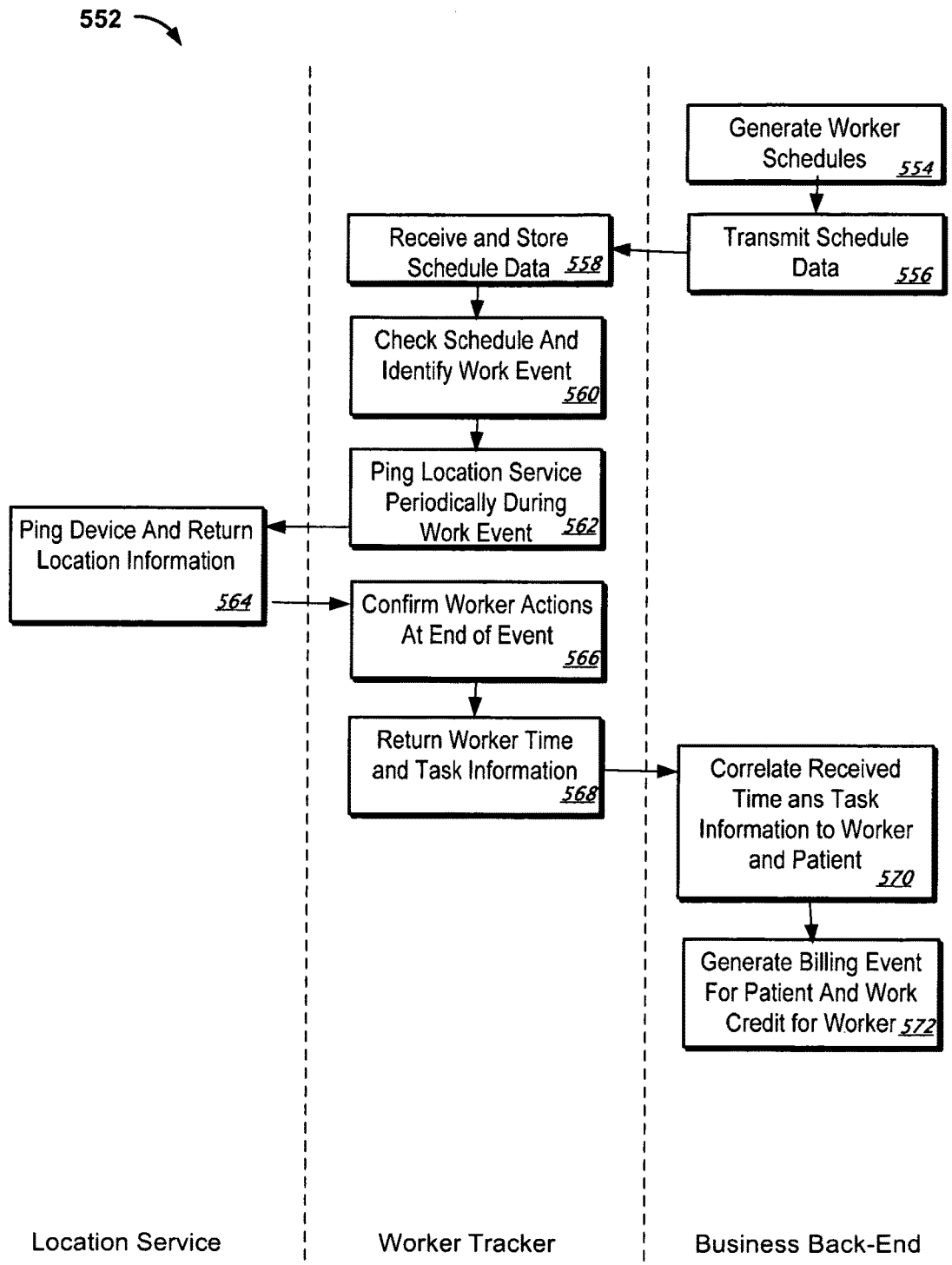

FIGS. 5B and 5C are swim lane diagrams showing actions for coordinating caregiver tracking with billing. The figures are generally directed to healthcare applications such as home healthcare. FIG. 5b generally shows interactions between a mobile client that is carried by a healthcare provider, a tracking server that is tasked with determining whether a healthcare provider met with patients according to a predetermined schedule, and a billing server that takes input from the tracking server to determine whether patients should be billed for care, and if so, to what extent they should be billed. The particular tasks assigned to each part of the system here are shown for illustrative purposes only, and various other portions of a system may take on these or other tasks.

At box 526, the billing server initially generates worker schedules for a certain time period, such as a workday. The schedules may be generated, for example, based on information from a healthcare system that indicates what services are to be provided to each patient. For example, the system may take input from physicians who have identified certain patients as being in need of certain treatments, such as at-home physical therapy or other similar care. Each patient need may be matched by the system with a particular caregiver that is identified within the system as being capable of providing for such a need. Matching of caregivers to patients may follow a number of other rules also, such as by efforts to minimize travel distances for caregivers.

At box 528, the billing server submits such schedule data to the tracking server, which receives the data at box 530 and formats it at box 532. For example, a tracking server may convert the data into a form of scheduling data that may be provided to a personal information manager (PIM) or similar software associated with each caregiver, so that they may be shown in a schedule for the care they are to provide during a particular day.

At box 534, a particular mobile client receives the schedule data and loads such data so that it can be reviewed by the caregiver during the day. As one example, the data may be provided to an application, similar to MICROSOFT OUT- LOOK, that provides a user interface with a scheduling application in a convenient manner.

Once the user arrives at a location, the mobile client may receive a location notification, such as at box 536. The location notification may be generated in a variety of manners. For example, a mobile client may itself monitor the movement relative to locations in the schedule and may generate the notification as soon as the mobile client comes near to a scheduled location. Alternatively, the worker may indicate when they have arrived at a location such as a patient's home, by launching an application for tracking locations. In such a manner, the worker may have better control over whether and when their location is tracked by the system.

At box 538, the location of the device is periodically tracked and recorded. For example, the device location may be tracked every minute, every five minutes, or every 10 minutes. Where the tracking is less frequent, the caregiver may be asked to manually confirm their presence near the mobile client, to ensure that the caregiver has not left the mobile client behind with the patient. Such periodic tracking of the location may repeat itself until the user leaves the particular location or otherwise indicates that the tracking should stop, such as by providing input to a control on a user interface of the client.

Where multiple patients are located at a single location, such as a group home, the caregiver can also activate the device so as to indicate that they are moving from caring for one patient to caring for another patient. Appropriate security mechanisms may be used to ensure that such care has occurred for each patient, such as by requiring the caregiver to photograph each patient as they start the session with the patient. Such images may also be used to defend the caregiver, such as if the patient or patient's family asserts that the care did not occur.

At box 540, the mobile client reports historic location data. Such reporting may occur by the instigation of the client, or by a request from the tracking server as shown at box 552. The reporting may occur, for example, periodically, such as every hour, several hours, or every work day. The location data may be returned in various formats, including a format that provides location and time for a location reading in a paired manner so that location and time can be cross-referenced against each other.

The tracking server records location data at box 544, and resolves the location data to the schedule data at box 546. Such resolution of the data may involve comparing time and location data that has been processed so as to correspond to each location at which a caregiver stopped during a workday. Particular data may be averaged or comparisons may be considered successful even without an exact match, to accommodate slight differences between the actual location of a user's home, and recorded locations, and differences in actual and planned schedule.

The tracking server may then report such information to the billing server which may check the actual schedule data against assignments for the day or other times. For example, if the billing server determines that a particular caregiver was to provide care to patient XYZ, the billing server may check to determine that the caregiver was at the home of patient XYZ during the appropriate time period. At box 550, the billing server bills the services to the various patients, and generates exception reports. Such reports, for example, may identify instances in which a caregiver's activities were determined to not match the planned schedule for the time, or to not match manual billing information entered by the caregiver Different forms of exceptions may be handled in different manners and may be considered to have different levels of seriousness. For example, a slight difference in timing may not be serious at all, and may result in a message being sent to a caregiver reminding them to work to their schedule or to provide information updating their schedule if they are falling behind. Alternatively, where more serious differences occur, such as indications that a caregiver left a patient's home for a short period during a visit, a message may be sent to the caregiver, asking them to explain what had happened. A manager may then receive the explanation and may follow-up to determine whether the caregiver acted appropriately and should be adequately compensated for providing the care. In more severe situations, such as where the system indicates that the caregiver never arrived at all a patient location, the system may delay compensation for the caregiver and may elevate the issue to a more senior manager.

FIG. 5C shows actions for a similar process 552, but from the view of various central services that may share information and interoperate so as to provide for accurate and convenient tracking of care given to patients in a healthcare system. Also, the example process is more naturally directed to a device having limited capabilities, such as a ZoomBak device, which responds to requests for time-location data from a central system rather than conducting any tracking itself.

The example process starts at box 554, where a business back-end system for a health network generates worker schedules for a work period such as a workday. The schedule may be generated as described above, by identifying various procedures that must be performed for patients during the period, and matching them with caregivers capable of performing the procedures. For example, a particular sort of nurse may be the only person in a network capable of providing a particular form of care, and that nurse may thus be matched solely with patients needing such care—preferably in a manner that minimizes the caregiver's need to drive across the city.

At box 556, the business back-end transmits the schedule data to a worker tracker subsystem, where the data is received and stored (box 558). The worker tracker subsystem may check the schedules and identify work events for the schedules. For example, the worker tracker subsystem may stay silent with respect to a particular worker until it determines, from the worker's schedule, that the worker should be at a particular patient's home. Such a determination may prevent the system from tracking the worker when the worker is on their own time (e.g., by providing agreed upon blackout periods). Security mechanisms may also be inserted into a system so that the worker cannot be tracked during such private periods, with a most natural security system being the worker's ability to turn off their tracking device or unplug it from a cigarette lighter in their automobile.

If the worker tracker determines that the worker is supposed to be at a particular location, it may ping the location service periodically during the time the worker is supposed to be working on site (box 562). The location service may respond by sending a ping to the device to get the device to respond with its location (box 564). Although the worker tracker may be provided with functionality to make the request directly, in this example the location service is a third party service such as that provided by a third-party such as Procon, Inc.

The location service then returns the location information, with or without processing, such as converting data in a proprietary format into standard lat/long data. If the latest ping was near the end of a scheduled working event, the worker tracker may confirm that the worker was on site the appropriate amount of time (box 566), and may return the worker time and task information to the business back-end subsystem (box 568) for billing purposes.

The business back-end subsystem may correlate the received time and task information to the worker and patient, in manners like those described above, to confirm whether the worker was on-site at the right place for the appropriate time period (box 570). If the worker acted properly, then the business back-end may generate a billing event for the patient and a work credit for the worker (box 572). The process 552 may then cycle back to the worker tracker identifying a next work event at a new time for the worker (e.g., the provision of care to a different patient at a different location), and may repeat the process of pinging the location of the worker during the time that the schedule shows they are to be on-site.

FIG. 6 is a conceptual diagram showing example database elements 600 for a healthcare billing system. In general, the elements 600 provide one example of a manner in which various records and fields may be organized in such a system. The example is provided for illustration only, and is not intended to limit the techniques, systems, or methods described here.

As shown, the elements 600 are organized into three general systems: a time tracker 602, an object tracker 604, and a billing system 606. In this implementation, the time tracker may be shown to have a single table (614) that correlates particular objects, such as patients, to particular procedures, and also provides start and end times for those procedures. Other objects may also be tracked, such as caregivers, so that time spent by a particular caregiver with respect to a particular procedure may be determined.

Object tracker 604 stores information about various objects that have been sensed in a facility, and times and locations associated with such sensing of the objects. A first table (608) correlates objects to locations (or to sensor IDs, where the sensors are in known locations), and the times that the objects were sensed in the particular locations. In this example, values for a particular object, such as a patient, are shown. In the example, the patient passes a first location on March 1 at about 9 p.m. and passes a second location about four minutes later, and a third location about three minutes after that. Each of the times and locations are tracked and are associated with the object (e.g., patient) in the table (608).

In another table (610), location identifiers and location names are correlated with each other. While computers may generally use simply the location identifiers in making computations, users of a system may prefer more intuitive location names. As a result, table 610 may be accessed when preparing information for reports or for other review by managers or others.

Table 612 provides active periods for particular objects, with respect to particular device IDs. Such tracking permits a single transponder to be used multiple times with different patients, and still maintain the capability to distinguish one patient from another in the system. For example, one patient may be associated with the transponder one week, while another patient can be associated the next week. Without tracking timing of patients in this manner, actions with respect to a particular transponder may not be able to be associated with any of several patients who used the transponder. In contrast, with tables 612, the identity of the patient may be determined by comparing the time or date on which a triggering event occurred with the device, to a time range during which the patient was staying at a particular facility ated with the transponder.

Billing system 606 may include numerous tables for tracking patient activity, billing, and other operations of a healthcare system or healthcare facility. Three example tables are shown here. Table 616 lists patients and all charges associated with those patients. The charges may follow various standard formats for billing codes, and may represent all chargeable events for a patient during a stay with the system. Such information may be used to form a complete bill for a patient stay at a facility. Table 618 lists the patient and all procedures performed on the patient. Such a table may not be necessary, and could be subsumed in some situations within particular charge numbers for the procedures. However, in certain implementations, a charge number may represent a procedure in general (e.g., an appendectomy), while the procedure number can represent the particular procedure performed on the particular patient (i.e., John Doe's appendectomy performed Jan. 1, 2000). Tracking of the particular procedure may permit a system, for example, to store particular data about the procedure, such as the caregivers that were involved in the procedure and the room in which the procedure was performed. Such information may be used, as described above, to track timing information for the procedure for purposes such as bill creation or bill verification.

Table 620 is a simplified form of a charge table—showing various charges to be applied for various chargeable events. In the example, the first entry may be the cost for a particular surgical procedure, while the second may be the cost for administering a pain medication to a patient. Other costs may represent hourly rates to be billed by certain caregivers. Various costs are shown here, as healthcare organizations frequently negotiate different price structures with different payors. The information in table 620 may be used, for example, when determining amounts to be included on a bill, such as by cycling through every charge associated with a particular patient during a particular time period, and matching a cost to each charge.

Figure 7:
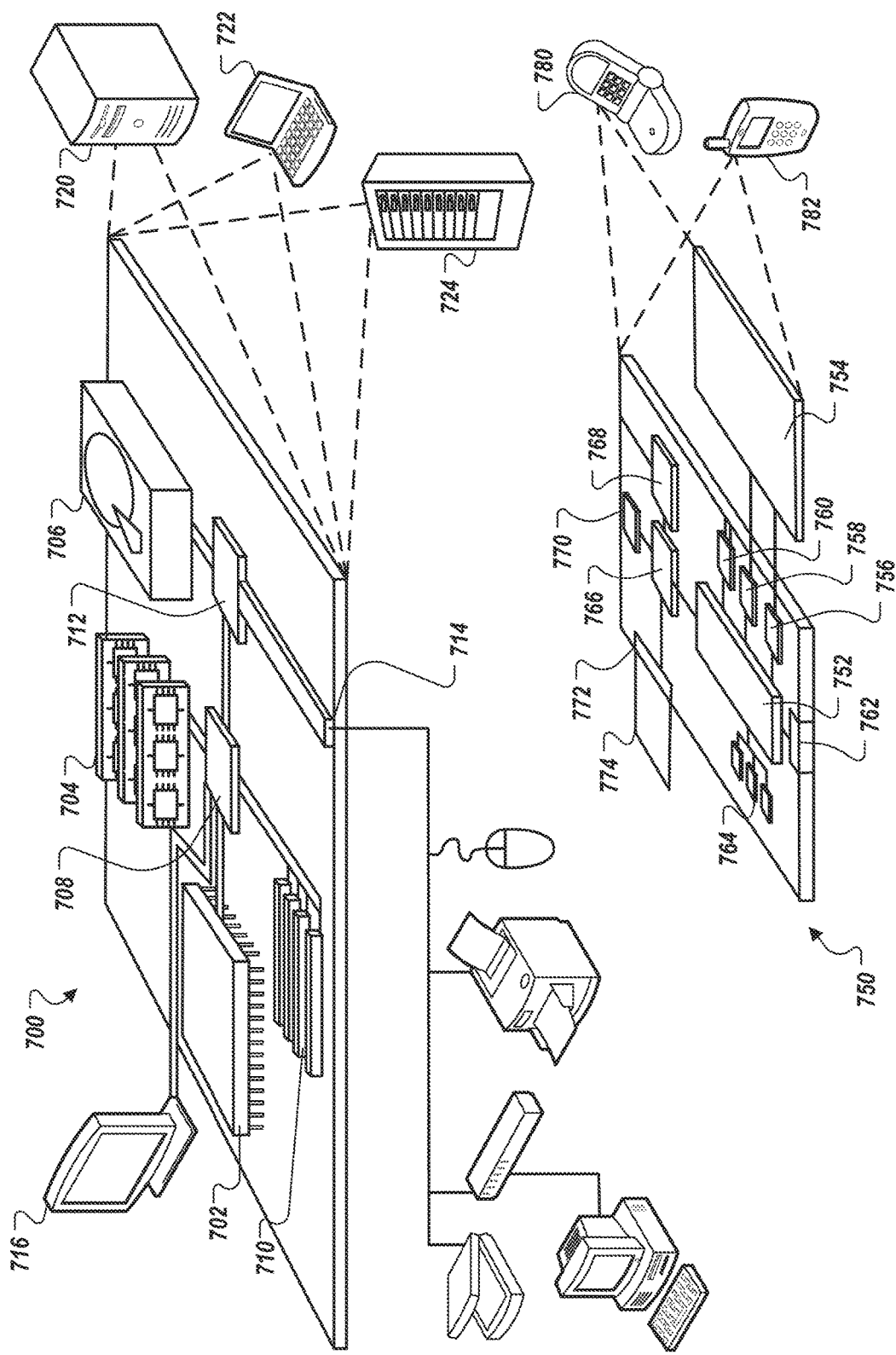
FIG. 7 is a block diagram of computing devices that can be used to implement the systems and methods described herein.

FIG. 7 is a block diagram of computing devices 700, 750 that can be used to implement the systems and methods described herein, as either a client or as a server or plurality of servers. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. The components shown here, their connections and relationships, and their functions, are meant to be exemplary only, and are not meant to limit implementations described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 704 stores information within the computing device 700. In one implementation, the memory 704 is a computer-readable medium. In one implementation, the memory 704 is a volatile memory unit or units. In another implementation, the memory 704 is a non-volatile memory unit or units.

The storage device 706 is capable of providing mass storage for the computing device 700. In one implementation, the storage device 706 is a computer-readable medium. In various different implementations, the storage device 706 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 704, the storage device 706, memory on processor 702, or a propagated signal.

The high-speed controller 708 manages bandwidth-intensive operations for the computing device 700, while the low speed controller 712 manages lower bandwidth-intensive operations. Such allocation of duties is exemplary only. In one implementation, the high-speed controller 708 is coupled to memory 704, display 716 (e.g., through a graphics processor or accelerator), and to high-speed expansion ports 710, which may accept various expansion cards (not shown). In the implementation, low-speed controller 712 is coupled to storage device 706 and low-speed expansion port 714. The low-speed expansion port, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. It may also be implemented as part of a rack server system 724. In addition, it may be implemented in a personal computer such as a laptop computer 722. Alternatively, components from computing device 700 may be combined with other components in a mobile device (not shown), such as device 750. Each of such devices may contain one or more of computing device 700, 750, and an entire system may be made up of multiple computing devices 700, 750 communicating with each other.

Computing device 750 includes a processor 752, memory 764, an input/output device such as a display 754, a communication interface 766, and a transceiver 768, among other components. The device 750 may also be provided with a storage device, such as a microdrive or other device, to provide additional storage. Each of the components 750, 752, 764, 754, 766, and 768, are interconnected using various buses, and several of the components may be mounted on a common motherboard or in other manners as appropriate.

The processor 752 can process instructions for execution within the computing device 750, including instructions stored in the memory 764. The processor may also include separate analog and digital processors. The processor may provide, for example, for coordination of the other components of the device 750, such as control of user interfaces, applications run by device 750, and wireless communication by device 750.

Processor 752 may communicate with a user through control interface 758 and display interface 756 coupled to a display 754. The display 754 may be, for example, a TFT LCD display or an OLED display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may be provided in communication with processor 752, so as to enable near area communication of device 750 with other devices. External interface 762 may provide, for example, for wired communication (e.g., via a docking procedure) or for wireless communication (e.g., via Bluetooth or other such technologies).

The memory 764 stores information within the computing device 750. In one implementation, the memory 764 is a computer-readable medium. In one implementation, the memory 764 is a volatile memory unit or units. In another implementation, the memory 764 is a non-volatile memory unit or units. Expansion memory 774 may also be provided and connected to device 750 through expansion interface 772, which may include, for example, a SIMM card interface. Such expansion memory 774 may provide extra storage space for device 750, or may also store applications or other information for device 750. Specifically, expansion memory 774 may include instructions to carry out or supplement the processes described above, and may include secure information also. Thus, for example, expansion memory 774 may be provided as a security module for device 750, and may be programmed with instructions that permit secure use of device 750. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, memory on processor 752, or a propagated signal.

Device 750 may communicate wirelessly through communication interface 766, which may include digital signal processing circuitry where necessary. Communication interface 766 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 768. In addition, short-range communication may occur, such as using a Bluetooth, WiFi, or other such transceiver (not shown). In addition, GPS receiver module 770 may provide additional wireless data to device 750, which may be used as appropriate by applications running on device 750.

Device 750 may also communicate audibly using audio codec 760, which may receive spoken information from a user and convert it to usable digital information. Audio codec 760 may likewise generate audible sound for a user, such as through a speaker, e.g., in a handset of device 750. Such sound may include sound from voice telephone calls, may include recorded sound (e.g., voice messages, music files, etc.) and may also include sound generated by applications operating on device 750.

The computing device 750 may be implemented in a number of different forms, as shown in the figure. For example, it may be implemented as a cellular telephone 780. It may also be implemented as part of a smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other categories of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back-end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Embodiments may be implemented, at least in part, in hardware or software or in any combination thereof. Hardware may include, for example, analog, digital or mixed-signal circuitry, including discrete components, integrated circuits (ICs), or application-specific ICs (ASICs). Embodiments may also be implemented, in whole or in part, in software or firmware, which may cooperate with hardware. Processors for executing instructions may retrieve instructions from a data storage medium, such as EPROM, EEPROM, NVRAM, ROM, RAM, a CD-ROM, a HDD, and the like. Computer program products may include storage media that contain program instructions for implementing embodiments described herein.

A number of implementations have been described. Nevertheless, it will be understood that various modifications may be made without departing from the spirit and scope of this disclosure. Accordingly, other implementations are within the scope of the claims.

What is claimed is:

1. A computer-implemented method, comprising:
 receiving, through the Internet and at a location identification server system that is programmed to identify when geographic locations of particular mobile devices match separately-identified geographic locations, electronic information that identifies locations for care to be provided to healthcare patients who are approved for care by a healthcare provider, and allocated amounts of care that correspond to anticipated durations of stay for one or more visits to the healthcare patients, wherein the healthcare patients have been previously enrolled with a system that coordinates providing of healthcare;
 receiving, by the location identification server system, location data generated by an electronic location identification service in response to receiving data generated by global positioning system (GPS) units of mobile devices that identify locations of particular healthcare providers when each instance of the location data is generated by respective ones of the GPS systems;
 comparing, with the location identification server system, digital data for the locations of the healthcare providers identified by the received location data obtained from GPS units, to the locations for care to be provided that were received by the location identification server system, so as to determine whether a location of a particular healthcare provider matches a particular location for care to be provided; and
 providing, by the location identification server system to a server system that coordinates providing of healthcare, electronic data that indicates an amount of care that corresponds to an actual duration of stay by the particular healthcare provider at the particular location for care to be provided, as a result of determining that the particular location for care to be provided matches the location of the particular healthcare provider responsive to the allocated amount of care, the electronic data being provided in response to receiving the electronic information that identifies the locations for care to be provided, wherein:
 the location data is received by the location identification server system (a) monitoring a schedule and location of the healthcare provider so that the monitoring transfers location information at an initial frequency when the schedule and location of the healthcare provider indicates that the healthcare provider is not actively with the patient, and (b) responsive to determining that the healthcare provider is actively with the patient, modifying the frequency with which the location data is obtained.

2. The computer-implemented method of claim 1, further comprising obtaining data regarding a location of the particular patient's residence, and comparing the location data to the location of the residence to determine an amount of time the particular healthcare provider spent at or near the particular patient's residence.

3. The computer-implemented method of claim 1, further comprising receiving data, periodically provided by the particular healthcare provider while at the location of the particular patient, indicating that the particular healthcare provider is currently physically operating a mobile electronic device, and correlating the received data with times during which the particular healthcare provider is scheduled to be at the location of the particular healthcare patient.

4. The computer-implemented method of claim 3, wherein the received data includes a digital image from the location of the particular healthcare patient captured at a time the digital image is submitted, and the location data is stored as time-location data pairs.

5. The computer-implemented method of claim 1, further comprising providing information to a mobile electronic device of the particular healthcare provider for generating a schedule of care, including location information for the healthcare patient.

6. The computer-implemented method of claim 5, wherein data for generating multiple schedules of care is provided to multiple mobile electronic devices according to a predetermined schedule.

7. The computer-implemented method of claim 1, wherein comparing the digital data for the locations of the healthcare providers to the locations for care to be provided comprises comparing the location data to a location of a scheduled appointment for the particular healthcare provider during a time indicated by the location data in order to determine whether the particular healthcare provider was at a scheduled location during a sufficient portion of the appointment.

8. The computer-implemented method of claim 7, further comprising computing an amount of a billable event based on elapsed time of the particular healthcare provider at the location of the particular healthcare patient.

9. The computer-implemented method of claim 1, wherein a single transmission of the electronic information combines data from multiple different indications of location for a particular mobile device.

10. A computer-implemented method, comprising:
providing over a computer network, for electronic presentation to a user of a mobile computing device, a schedule for treatment of one or more healthcare patients;
generating location data for the mobile computing device that digitally represents locations of the one or more healthcare patients in response to receiving location data from a global positioning system (GPS) unit of the mobile computing device identifying locations of the one or more healthcare patients; and
processing the location data at a central location identification server system by comparing the location data from the GPS unit to locations associated with the one or more healthcare patients, which locations were supplied to a central service over the Internet with allocated amounts of care that correspond to anticipated durations of stay by healthcare providers with particular ones of the patients, and providing duration and location data based on determining that the user of the mobile computing device was present at the locations of the one or more healthcare patients for whom an amount of care has been allocated, the duration and location data being generated by electronically filtering the location data using data supplied to the central location identification server system that identifies locations of healthcare patients, so as to identify information associated with locations within a set distance of the location of the one or more healthcare patients, and being supplied by the central location identification server system to a healthcare billing system as data indicating a duration the mobile computing device was electronically determined to be at one of the locations of the one or more healthcare patients, for generating automatic billing for care provided to the one or more healthcare patients, wherein:
the location data is received by the location identification server system (a) monitoring a schedule and location of the healthcare provider so that the monitoring transfers location information at an initial frequency when the schedule and location of the healthcare provider indicates that the healthcare provider is not actively with the patient, and (b) responsive to determining that the healthcare provider is actively with the patient, modifying the frequency with which the location data is obtained.

11. The method of claim 10, wherein providing the schedule comprises presenting on a graphical user interface one or more maps showing the locations of the one or more healthcare patients.

12. The method of claim 10, further comprising automatically downloading schedule data for generating the schedule, without intervention by the user.

13. The method of claim 10, further comprising automatically seeking manual input from the user during a time period when the user is supposed to be at the locations of the one or more patients.

14. The method of claim 13, wherein the manual input comprises biometric input from the user.

15. The method of claim 14, further comprising submitting data for the biometric input and location data together to the central service for verification that the user was actually at a patient location during a particular time period.

16. The method of claim 10, further comprising receiving from the central service an indication that treatment of a patient at a scheduled location has been confirmed for the user.

17. A computer-implemented performance verification system, comprising:
a database storing location data that represents geographic locations for healthcare patients and received from a third party over the Internet, along with indications, for each of the healthcare patients, of allocated amounts of care that include anticipated durations of stay for one or more visits to the healthcare patients;
a server-based interface arranged to receive location data generated by global positioning system (GPS) units of mobile electronic devices associated with healthcare providers, wherein the location data indicates locations of the devices electronically determined using the GPS units at times the healthcare providers are physically at the locations; and one or more processors operating on one or more computer servers programmed to electronically filter the received location data using the data representing geographic locations for healthcare patients, so as to identify data associated with locations within set distances of the geographic locations for healthcare patients, to use the identified data to determine durations that mobile devices were electronically determined to be within set distances of particular ones of the geographic locations for healthcare patients, and to provide data to a remote healthcare management system that is separate from the performance verification system, the provided data indicating a determination that the received location data matches the stored location data and allocated amount of care that was submitted separately from the location data, so as to allow the remote healthcare management system to generate charges for care provided to the healthcare patients, wherein:

the location data is received by the system (a) monitoring a schedule and location of the healthcare provider so that the monitoring transfers location information at an initial frequency when the schedule and location of the healthcare provider indicates that the healthcare provider is not actively with the patient, and (b) responsive to determining that the healthcare provider is actively with the patient, modifying the frequency with which the location data is obtained.

18. The system of claim 17, further comprising an interface to receive historical location information from mobile devices corresponding to the healthcare providers and to provide the location information for comparison with the stored location data.

19. The system of claim 17, further comprising medical record storage for the healthcare patients, and an interface to provide medical record information from medical record storage to verified healthcare providers over a wireless network.

20. The system of claim 17, further comprising an interface programmed to periodically request location information from a plurality of mobile devices associated with the healthcare providers.

21. The system of claim 17, further comprising a schedule generator programmed to identify patients in need of care and to produce schedules for the healthcare providers including location information for the healthcare patients.

22. A computer-implemented system, including one or more non-transitory computer-readable storage media comprising:

one or more computer processors;

memory in communication with the one or more processors and storing time-location data for a plurality of healthcare providers in a healthcare system, the time-location information generated by global positioning system (GPS) units of mobile devices of the healthcare providers and correlating a particular physical location of a particular healthcare provider with a particular time the particular healthcare provider was at the particular physical location;

memory in communication with the one or more processors and storing location data for a plurality of healthcare patients with correlated data that indicates allocated levels of care for the healthcare patients corresponding to intended durations of stay by healthcare providers at locations of the healthcare patients, the location information and the information that indicates allocated levels of care being provided to the computer-implemented system over the Internet from a third party;

a comparison module, executable on the one or more processors, and programmed to determine whether time-location data for particular ones of the healthcare providers matches location data for which an allocated level of care has been provided; and memory storing instructions, executable on the one or more processors, for providing, to a healthcare management system and through a network, data that identifies whether comparisons made by the comparison module indicate that care was provided to a particular patient for whom an allocated level of care has been provided, wherein:

the location data is received by the system (a) monitoring a schedule and location of the healthcare provider so that the monitoring transfers location information at an initial frequency when the schedule and location of the healthcare provider indicates that the healthcare provider is not actively with the patient, and (b) responsive to determining that the healthcare provider is actively with the patient, modifying the frequency with which the location data is obtained.

23. A computer-implemented method, comprising:

receiving, through the Internet and at a location identification server system that is programmed to identify when geographic locations of particular mobile devices match separately-identified geographic locations, electronic information that identifies locations for care to be provided to healthcare patients who are approved for care by a healthcare provider, and allocated amounts of care that correspond to anticipated durations of stay for one or more visits to the healthcare patients, wherein the healthcare patients have been previously enrolled with a system that coordinates providing of healthcare;

receiving, by the location identification server system, location data generated by an electronic location identification service in response to receiving data generated by global positioning system (GPS) units of mobile devices that identify locations of particular healthcare providers when each instance of the location data is generated by respective ones of the GPS systems;

comparing, with the location identification server system, digital data for the locations of the healthcare providers identified by the received location data obtained from GPS units, to the locations for care to be provided that were received by the location identification server system, so as to determine whether a location of a particular healthcare provider matches a particular location for care to be provided; and providing, by the location identification server system to a server system that coordinates providing of healthcare, electronic data that indicates an amount of care that corresponds to an actual duration of stay by the particular healthcare provider at the particular location for care to be provided, as a result of determining that the particular location for care to be provided matches the location of the particular healthcare provider responsive to the allocated amount of care, the electronic data being provided in response to receiving the electronic information that identifies the locations for care to be provided, wherein:

the location data is received by the location identification server system (a) monitoring a schedule and location of the healthcare provider so that the monitoring transfers location information at an initial frequency when the schedule and location of the healthcare provider indicates that the healthcare provider is not actively with the patient, and (b) responsive to determining that the healthcare provider is actively with the patient, modifying the frequency with which the location data is obtained.

24. The computer-implemented method of claim 23, further comprising obtaining data regarding a location of the particular patient's residence, and comparing the location data to the location of the residence to determine an amount of time the particular healthcare provider spent at or near the particular patient's residence.

25. The computer-implemented method of claim 24, wherein the received data includes a digital image from the location of the particular healthcare patient captured at a time the digital image is submitted, and the location data is stored as time-location data pairs.

26. The computer-implemented method of claim 23, further comprising providing information to a mobile electronic device of the particular healthcare provider for generating a schedule of care, including location information for the healthcare patient.

27. The computer-implemented method of claim 23, wherein a single transmission of the electronic information combines data from multiple different indications of location for a particular mobile device.

* * * * *